US009629627B2

(12) United States Patent
Kostrzewski et al.

(10) Patent No.: US 9,629,627 B2

(45) Date of Patent: Apr. 25, 2017

(54) SURGICAL APPARATUS

(71) Applicant: Covidien LP, Mansfield, MA (US)

(72) Inventors: Stanislaw Kostrzewski, Newtown, CT (US); Ernest Aranyi, Easton, CT (US)

(73) Assignee: Coviden LP, Mansfield, MA (US)

( * ) Notice: Subject to any disclaimer, the term of this patent is extended or adjusted under 35 U.S.C. 154(b) by 576 days.

(21) Appl. No.: 14/166,294

(22) Filed: Jan. 28, 2014

(65) Prior Publication Data

US 2015/0209037 A1 Jul. 30, 2015

(51) Int. Cl.

*A61B 17/072* (2006.01)
*A61B 17/068* (2006.01)
*A61B 17/00* (2006.01)

(52) U.S. Cl.

CPC ........ *A61B 17/072* (2013.01); *A61B 17/0682* (2013.01); *A61B 2017/0046* (2013.01); *A61B 2017/07214* (2013.01); *A61B 2017/07257* (2013.01); *A61B 2017/07271* (2013.01)

(58) Field of Classification Search

CPC .............. A61B 17/0682; A61B 17/072; A61B 2017/0046; A61B 2017/07214; A61B 2017/07257; A61B 2017/07271

USPC ..................... 227/176.1, 178.1, 175.1, 177.1

See application file for complete search history.

(56) References Cited

U.S. PATENT DOCUMENTS 2,887,111 A 5/1959 Diaz
3,079,606 A 3/1963 Bobrov et al.
3,490,675 A 1/1970 Green et al.
4,429,695 A 2/1984 Green
4,505,414 A 3/1985 Filipi
4,589,413 A 5/1986 Malyshev et al.
4,602,634 A 7/1986 Barkley
4,608,981 A 9/1986 Rothfuss et al.
(Continued)

FOREIGN PATENT DOCUMENTS

DE 2744824 A1 4/1978
DE 2903159 A1 7/1980
(Continued)

OTHER PUBLICATIONS

European Search Report corresponding to EP 14199704.9 dated May 8, 2015; 8 pages.
(Continued)

*Primary Examiner* — Hemant M Desai
*Assistant Examiner* — Valentin Neacsu

(57) ABSTRACT

A surgical stapling apparatus is provided. The surgical stapling apparatus includes an actuating device including an elongated shaft. A tool assembly is disposed on a distal end of the shaft. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first and second jaw members includes a cantilever at a proximal end thereof. A firing cam bar assembly is slidably disposed within the tool assembly and includes a cam surface configured to engage the cantilever to move the first and second jaw member towards the approximated position and a distal end configured to deploy the plurality of surgical fasteners from the cartridge assembly.

22 Claims, 28 Drawing Sheets

(56) References Cited

U.S. PATENT DOCUMENTS 4,610,383 A 9/1986 Rothfuss et al.
4,633,861 A 1/1987 Chow et al.
4,633,874 A 1/1987 Chow et al.
4,671,445 A 6/1987 Barker et al.
4,703,887 A 11/1987 Clanton et al.
4,728,020 A 3/1988 Green et al.
4,784,137 A 11/1988 Kulik et al.
4,815,465 A 3/1989 Alvarado
4,863,088 A 9/1989 Redmond et al.
4,892,244 A 1/1990 Fox et al.
4,991,764 A 2/1991 Mericle
5,040,715 A 8/1991 Green et al.
5,065,929 A 11/1991 Schulze et al.
5,074,454 A 12/1991 Peters
5,083,695 A 1/1992 Foslien et al.
5,108,403 A 4/1992 Stern
5,111,987 A 5/1992 Moeinzadeh et al.
5,129,570 A 7/1992 Schulze et al.
5,141,144 A 8/1992 Foslien et al.
5,156,633 A 10/1992 Smith
5,170,925 A 12/1992 Madden et al.
5,217,460 A 6/1993 Knoepfler
5,219,354 A 6/1993 Choudhury et al.
RE34,519 E 1/1994 Fox et al.
5,282,807 A 2/1994 Knoepfler
5,307,976 A 5/1994 Olson et al.
5,312,023 A 5/1994 Green et al.
5,318,221 A 6/1994 Green et al.
5,326,013 A 7/1994 Green et al.
5,332,142 A 7/1994 Robinson et al.
5,364,003 A 11/1994 Williamson, IV
5,376,095 A 12/1994 Ortiz
5,381,943 A 1/1995 Allen et al.
5,383,880 A 1/1995 Hooven
5,395,033 A 3/1995 Byrne et al.
5,395,034 A 3/1995 Allen et al.
5,397,046 A 3/1995 Savage et al.
5,397,324 A 3/1995 Carroll et al.
5,407,293 A 4/1995 Crainich
5,415,334 A 5/1995 Williamson et al.
5,415,335 A 5/1995 Knodell, Jr.
5,417,361 A 5/1995 Williamson, IV
5,431,323 A 7/1995 Smith et al.
5,433,721 A 7/1995 Hooven et al.
5,447,265 A 9/1995 Vidal et al.
5,452,837 A 9/1995 Williamson, IV et al.
5,464,300 A 11/1995 Crainich
5,465,895 A 11/1995 Knodel et al.
5,467,911 A 11/1995 Tsuruta et al.
5,470,007 A 11/1995 Plyley et al.
5,470,010 A 11/1995 Rothfuss et al.
5,474,566 A 12/1995 Alesi et al.
5,476,206 A 12/1995 Green et al.
5,484,451 A 1/1996 Akopov et al.
5,485,947 A 1/1996 Olson et al.
5,487,500 A 1/1996 Knodel et al.
5,489,058 A 2/1996 Plyley et al.
5,507,426 A 4/1996 Young et al.
5,518,163 A 5/1996 Hooven
5,518,164 A 5/1996 Hooven
5,529,235 A 6/1996 Boiarski et al.
5,531,744 A 7/1996 Nardella et al.
5,535,934 A 7/1996 Boiarski et al.
5,535,937 A 7/1996 Boiarski et al.
5,540,375 A 7/1996 Bolanos et al.
5,551,622 A 9/1996 Yoon
5,553,765 A 9/1996 Knodel et al.
5,562,239 A 10/1996 Boiarski et al.
5,562,241 A 10/1996 Knodel et al.
5,562,682 A 10/1996 Oberlin et al.
5,564,615 A 10/1996 Bishop et al.
5,573,543 A 11/1996 Akopov et al.
5,577,654 A 11/1996 Bishop
5,586,711 A 12/1996 Plyley et al.
5,588,580 A 12/1996 Paul et al.
5,588,581 A 12/1996 Conlon et al.
5,597,107 A 1/1997 Knodel et al.
5,601,224 A 2/1997 Bishop et al.
5,607,095 A 3/1997 Smith et al.
5,624,452 A 4/1997 Yates
5,626,587 A 5/1997 Bishop et al.
5,628,446 A 5/1997 Geiste et al.
5,630,539 A 5/1997 Plyley et al.
5,630,540 A 5/1997 Blewett
5,630,541 A 5/1997 Williamson, IV et al.
5,632,432 A 5/1997 Schulze et al.
5,634,584 A 6/1997 Okorocha et al.
5,636,780 A 6/1997 Green et al.
5,645,209 A 7/1997 Green et al.
5,647,526 A 7/1997 Green et al.
5,649,957 A 7/1997 Levin
5,653,374 A 8/1997 Young et al.
5,653,721 A 8/1997 Knodel et al.
5,655,698 A 8/1997 Yoon
5,657,921 A 8/1997 Young et al.
5,658,300 A 8/1997 Bito et al.
5,662,258 A 9/1997 Knodel et al.
5,662,259 A 9/1997 Yoon
5,662,260 A 9/1997 Yoon
5,662,662 A 9/1997 Bishop et al.
5,662,666 A 9/1997 Onuki et al.
5,665,097 A 9/1997 Baker et al.
5,665,100 A 9/1997 Yoon
5,667,517 A 9/1997 Hooven
5,669,544 A 9/1997 Schulze et al.
5,673,840 A 10/1997 Schulze et al.
5,673,841 A 10/1997 Schulze et al.
5,673,842 A 10/1997 Bittner et al.
5,676,674 A 10/1997 Bolanos et al.
5,680,982 A 10/1997 Schulze et al.
5,690,269 A 11/1997 Bolanos et al.
5,690,653 A 11/1997 Richardson et al.
5,692,668 A 12/1997 Schulze et al.
5,697,542 A 12/1997 Knodel et al.
5,704,534 A 1/1998 Huitema et al.
5,709,334 A 1/1998 Sorrentino et al.
5,711,472 A 1/1998 Bryan
5,713,505 A 2/1998 Huitema
5,716,366 A 2/1998 Yates
5,728,110 A 3/1998 Vidal et al.
5,735,848 A 4/1998 Yates et al.
5,743,456 A 4/1998 Jones et al.
5,749,893 A 5/1998 Vidal et al.
5,752,644 A 5/1998 Bolanos et al.
5,762,255 A 6/1998 Chrisman et al.
5,762,256 A 6/1998 Mastri et al.
5,769,303 A 6/1998 Knodel et al.
5,772,099 A 6/1998 Gravener
5,779,130 A 7/1998 Alesi et al.
5,779,131 A 7/1998 Knodel et al.
5,779,132 A 7/1998 Knodel et al.
5,782,396 A 7/1998 Mastri et al.
5,782,397 A 7/1998 Koukline
5,797,536 A 8/1998 Smith et al.
5,797,537 A 8/1998 Oberlin et al.
5,797,538 A 8/1998 Heaton et al.
5,810,811 A 9/1998 Yates et al.
5,810,855 A 9/1998 Rayburn et al.
5,816,471 A 10/1998 Plyley et al.
5,817,109 A 10/1998 McGarry et al.
5,820,009 A 10/1998 Melling et al.
5,823,066 A 10/1998 Huitema et al.
5,826,776 A 10/1998 Schulze et al.
5,829,662 A 11/1998 Allen et al.
5,833,695 A 11/1998 Yoon
5,836,147 A 11/1998 Schnipke
5,862,972 A 1/1999 Green et al.
5,865,361 A 2/1999 Milliman et al.
5,871,135 A 2/1999 Williamson, IV et al.
5,897,562 A 4/1999 Bolanos et al.
5,901,895 A 5/1999 Heaton et al.
5,911,353 A 6/1999 Bolanos et al.
5,918,791 A 7/1999 Sorrentino et al.
5,941,442 A 8/1999 Geiste et al.

(56) References Cited

U.S. PATENT DOCUMENTS

| | | | |
|---|---|---|---|
| 5,954,259 | A | 9/1999 | Viola et al. |
| 6,001,120 | A | 12/1999 | Levin |
| 6,004,335 | A | 12/1999 | Vaitekunas et al. |
| 6,010,054 | A | 1/2000 | Johnson et al. |
| 6,013,028 | A | 1/2000 | Jho et al. |
| 6,032,849 | A | 3/2000 | Mastri et al. |
| 6,036,714 | A | 3/2000 | Chin |
| 6,079,606 | A | 6/2000 | Milliman et al. |
| 6,099,537 | A | 8/2000 | Sugai et al. |
| 6,109,500 | A | 8/2000 | Alli et al. |
| 6,197,017 | B1 | 3/2001 | Brock et al. |
| 6,202,917 | B1 | 3/2001 | Weaver et al. |
| 6,241,139 | B1 | 6/2001 | Milliman et al. |
| 6,241,740 | B1 | 6/2001 | Davis et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,269,977 | B1 | 8/2001 | Moore |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,439,446 | B1 | 8/2002 | Perry et al. |
| 6,443,973 | B1 | 9/2002 | Whitman |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,656,193 | B2 | 12/2003 | Grant et al. |
| 6,679,895 | B1 | 1/2004 | Sancoff et al. |
| 6,698,643 | B2 | 3/2004 | Whitman |
| 6,704,210 | B1 | 3/2004 | Myers |
| 6,722,552 | B2 | 4/2004 | Fenton, Jr. |
| 6,755,815 | B2 | 6/2004 | Schultz |
| 6,761,725 | B1 | 7/2004 | Grayzel et al. |
| 7,131,978 | B2 | 11/2006 | Sancoff et al. |
| 7,308,998 | B2 | 12/2007 | Mastri et al. |
| 2001/0034535 | A1 | 10/2001 | Schultz |
| 2003/0065351 | A1 | 4/2003 | Hess et al. |
| 2004/0019355 | A1 | 1/2004 | Mehdizadeh |
| 2004/0094597 | A1 | 5/2004 | Whitman et al. |
| 2004/0243151 | A1 | 12/2004 | Demmy et al. |
| 2005/0119669 | A1 | 6/2005 | Demmy |
| 2005/0216055 | A1 | 9/2005 | Scirica et al. |
| 2006/0100644 | A1* | 5/2006 | Viola ............... A61B 17/07207 606/142 |
| 2006/0168531 | A1 | 7/2006 | Sato |
| 2007/0114262 | A1* | 5/2007 | Mastri ................ A61B 17/0684 227/176.1 |
| 2007/0175950 | A1* | 8/2007 | Shelton ............ A61B 17/07207 227/176.1 |
| 2008/0078808 | A1* | 4/2008 | Hess .................. A61B 17/0644 227/181.1 |
| 2009/0206138 | A1* | 8/2009 | Smith .............. A61B 17/07207 227/176.1 |
| 2009/0218384 | A1* | 9/2009 | Aranyi ............. A61B 17/07207 227/176.1 |
| 2009/0306708 | A1* | 12/2009 | Shah ................ A61B 17/07207 606/219 |
| 2012/0080493 | A1* | 4/2012 | Shelton, IV ........... A61B 90/92 227/176.1 |
| 2012/0305627 | A1* | 12/2012 | Milliman ......... A61B 17/07207 227/176.1 |

FOREIGN PATENT DOCUMENTS

| | | | |
|---|---|---|---|
| DE | 3114135 | A1 | 10/1982 |
| DE | 4213426 | A1 | 10/1992 |
| DE | 4300307 | A1 | 7/1994 |
| EP | 0041022 | A1 | 12/1981 |
| EP | 0136950 | A2 | 4/1985 |
| EP | 0140552 | A2 | 5/1985 |
| EP | 0213817 | A1 | 3/1987 |
| EP | 0220029 | A1 | 4/1987 |
| EP | 0273468 | A2 | 7/1988 |
| EP | 0324166 | A2 | 7/1989 |
| EP | 0324635 | A1 | 7/1989 |
| EP | 0324637 | A1 | 7/1989 |
| EP | 0324638 | A1 | 7/1989 |
| EP | 0365153 | A1 | 4/1990 |
| EP | 0369324 | A1 | 5/1990 |
| EP | 0373762 | A1 | 6/1990 |
| EP | 0380025 | A2 | 8/1990 |
| EP | 0399701 | A1 | 11/1990 |
| EP | 0449394 | A2 | 10/1991 |
| EP | 0484677 | A1 | 5/1992 |
| EP | 0489436 | A1 | 6/1992 |
| EP | 0503662 | A1 | 9/1992 |
| EP | 0514139 | A2 | 11/1992 |
| EP | 0537572 | A2 | 4/1993 |
| EP | 0539762 | A1 | 5/1993 |
| EP | 0545029 | A1 | 6/1993 |
| EP | 0552050 | A2 | 7/1993 |
| EP | 0552423 | A2 | 7/1993 |
| EP | 0579038 | A1 | 1/1994 |
| EP | 0589306 | A2 | 3/1994 |
| EP | 0591946 | A1 | 4/1994 |
| EP | 0592243 | A2 | 4/1994 |
| EP | 0593920 | A1 | 4/1994 |
| EP | 0598202 | A1 | 5/1994 |
| EP | 0621009 | A1 | 10/1994 |
| EP | 0656188 | A2 | 6/1995 |
| EP | 0666057 | A2 | 8/1995 |
| EP | 0705571 | A1 | 4/1996 |
| EP | 0760230 | A1 | 3/1997 |
| EP | 2130499 | A1 | 12/2009 |
| FR | 2542188 | A1 | 9/1984 |
| FR | 2660851 | A1 | 10/1991 |
| FR | 2681775 | A1 | 4/1993 |
| GB | 216559 | A | 5/1924 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51-149985 | | 12/1976 |
| RU | 659146 | | 4/1979 |
| RU | 728848 | | 4/1980 |
| RU | 980703 | | 12/1982 |
| RU | 990220 | | 1/1983 |
| WO | 08302247 | | 7/1983 |
| WO | 89/10094 | A1 | 11/1989 |
| WO | 9210976 | A1 | 7/1992 |
| WO | 9308754 | A1 | 5/1993 |
| WO | 9314706 | A1 | 8/1993 |
| WO | 2004/032754 | A2 | 4/2004 |

OTHER PUBLICATIONS

European Office Action corresponding to counterpart Int'l Appln. No. EP 14 19 9704.9, dated Apr. 26, 2016.

European Search Report 08251159.3-1526 dated Nov. 11, 2008.

Definition of "contiguous" according to Merriam-Webster; http:/www.merriam-webster.com/dictionary/contiguous.

* cited by examiner 20
24a
32
34
36
24b
22b 22a
26a
18
26b
52
54
57
28b
28a
66a
66b
11
9
13
19
64b
64a
10
17
60
62
56
15
14

34
36
40
39
38
4
44
45a
45b
37a
37b
48a
48b
42a
42b
"B"
"T"
33

110
116
120
124a
122a
126a
132
174
184
140
134
137
128a
126b
156
117
119
113
114
15
122b
124b
188
126b 122b
190b
190b 176
189
164
184
172
186
156
173
154
152
151
142
171
136
190a
191

110
41
114
117
113
187

185
164
110
193
195
187
114

SURGICAL APPARATUS

BACKGROUND

Technical Field

The present disclosure relates to a surgical apparatus. More specifically, the present disclosure relates to a surgical stapler including firing assemblies configured to control tissue gap distance between jaw members of the stapler when the jaw members are in a clamping configuration and the surgical stapler is fired.

Description of Related Art

Surgical staplers configured to clamp and staple tissue are known. Such staplers may include a tool assembly that is supported at a distal end of a shaft of the stapler. The tool assembly may, for example, include an anvil and a cartridge including a plurality of fasteners that are configured to staple tissue (e.g., occlusion of vascular structure during a transplant procedure).

To staple tissue with such staplers, tissue can be positioned between the cartridge and anvil, and the anvil can be approximated towards the cartridge to clamp the tissue. Once tissue is clamped, the stapler can be fired to advance the drive assembly of the stapler distally through the cartridge to eject the plurality of surgical fasteners sequentially from the cartridge to staple tissue.

In addition to the mechanisms recited to fire the plurality of fasteners, conventional staplers may further include a structure configured to control tissue gap distance between the anvil and the cartridge of the tool assembly during firing of the stapler.

While the aforementioned staplers may be satisfactory for the above uses, there may exist a need for a simpler design for firing surgical fasteners and/or approximating a cartridge towards an anvil. There is also a need for a firing assembly that takes up less space, as well as a need for an alternative approximation assembly and/or method.

SUMMARY

An aspect of the present disclosure provides a surgical stapling apparatus. The surgical stapling apparatus includes an actuating device including an elongated shaft. A tool assembly is disposed on a distal end of the shaft. The tool assembly may be removably couplable to the distal end of the shaft of the surgical stapling apparatus. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first and second jaw members includes a cantilever at a proximal end thereof. The cantilever may be in the form of a bridge that extends transverse in relation to a longitudinal axis defined through the shaft of the surgical stapling apparatus. A firing cam bar assembly is slidably disposed within the tool assembly. The firing cam bar assembly includes a cam surface configured to engage the cantilever to move the first and second jaw member towards the approximated position and a distal end configured to deploy the plurality of surgical fasteners from the cartridge as the firing cam bar assembly is translated distally through the tool assembly.

The firing cam bar assembly may include a first firing cam bar having an elongated configuration and a distal portion defining the cam surface. The surgical stapler may further include a second firing cam bar having an elongated configuration and a distal portion defining the cam surface, the second firing cam bar seated within the first firing cam bar. The cartridge may include a plurality of pushers and the distal portions of the first and second firing cam bars are configured to contact the plurality of pushers of the cartridge to deploy the plurality of surgical fasteners from the cartridge.

The cam surface of the firing cam bar assembly may include a first cam portion disposed distally and at an angle in relation to a second cam portion. The second cam portion of the cam surface may taper inwardly toward a proximal end of the firing cam bar assembly.

A resilient member may be provided on the cartridge for biasing the cartridge radially away from the anvil. The resilient member may include a proximal end that is coupled to a proximal end of the cartridge and a distal end that is positioned to contact at least a portion of the anvil. The proximal end of the resilient member may include two finger portions that are seated within two corresponding apertures defined at the proximal end of the cartridge.

An aspect of the present disclosure provides a reload configured for use with a surgical stapling apparatus. The reload includes a shaft including a proximal end, which is adapted to couple to a surgical apparatus, and distal end. A tool assembly is disposed on the distal end of the shaft. The tool assembly includes a first jaw member supporting a cartridge assembly having a plurality of surgical fasteners, and a second jaw member supporting an anvil. The first jaw member is movable in relation to the second jaw member between a spaced position and an approximated position. One of the first and second jaw members includes a cantilever at a proximal end thereof. The cantilever may be in the form of a bridge that extends transverse in relation to a longitudinal axis defined through the shaft of the surgical stapling apparatus. A firing cam bar assembly is slidably disposed within the tool assembly. The firing cam bar assembly includes a cam surface configured to engage the cantilever to move the first and second jaw member towards the approximated position and a distal end configured to deploy the plurality of surgical fasteners from the cartridge as the firing cam bar assembly is translated distally through the tool assembly.

An aspect of the present disclosure provides a surgical stapling apparatus. The surgical stapling apparatus includes an actuating device including an elongated shaft. A tool assembly is disposed on a distal end of the shaft. The tool assembly is removably couplable to the distal end of the shaft of the surgical stapling apparatus. The tool assembly includes a first jaw member supporting a cartridge assembly having a plurality of fasteners and a sled positioned to eject the fasteners from the cartridge assembly and a second jaw member supporting an anvil. The first jaw member is movable in relation to the second jaw member between spaced and approximated positions. A sled pusher assembly includes a sled pusher having a distal end configured to engage the sled of the cartridge assembly. A drive beam assembly includes a latch assembly having a latch releasably coupled to the sled pusher assembly. Distal translation of the drive beam assembly from a refracted position towards an advanced position effects movement of the first and second jaw members to the approximated position and disengages the latch of the latch assembly from the sled pusher assembly to facilitate distal movement of the sled pusher independently of the drive beam assembly. Distal movement of the sled pusher independently of the drive beam assembly also advances the distal end of the sled pusher into engagement with the sled of the cartridge assembly to eject the plurality of fasteners from the cartridge assembly.

The latch assembly may include a collar which is coupled to a proximal end of the drive beam assembly and may include an aperture configured to receive a support member of the sled pusher assembly. The support member of the sled pusher assembly may include at least one aperture that is configured to receive the latch of the latch assembly.

The drive beam assembly may include an I-beam having a sidewall defining a notch, the sled pusher being received within the notch. The I-beam may be positioned to cam the first and second jaw members to the approximated position when the drive beam assembly is translated distally.

The latch assembly may include at least one spring configured to bias the latch of the latch assembly into the aperture defined in the support member of the sled pusher assembly. The aperture of the support member may be defined by a proximal wall portion of the sled pusher assembly. The proximal wall portion may be configured to engage the latch of the latch assembly to maintain the drive beam assembly and the sled pusher coupled with one another.

The elongated shaft may include upper and lower housing portions, and at least one of the upper and lower housing portions includes at least one stop member configured to contact a proximal end of the collar of the latch assembly when the drive beam assembly is translated distally. The latch may include a lateral offset extension, and wherein at least one of the upper and lower housing portions of the elongated shaft includes at least one ramp portion configured to be engaged by the lateral offset extension to effect movement of the latch out of engagement with the proximal wall portion when the drive beam assembly is moved distally so as to allow the sled pusher assembly to move distally in relation to the drive beam assembly.

A resilient member may be provided on the cartridge for biasing the cartridge assembly radially away from the anvil. The resilient member may include a bottom portion that is coupled to a proximal end of the cartridge and a top portion that is positioned to contact at least a portion of the anvil. The bottom portion of the resilient member may be seated within a corresponding slot defined at the proximal end of the cartridge assembly. The bottom portion of the resilient member may include at least one detent that couples to a corresponding indent disposed on the cartridge assembly adjacent the slot.

An aspect of the present disclosure provides a reload configured for use with a surgical stapling apparatus. The reload includes a shaft including a proximal end and distal end. The proximal end adapted to couple to a surgical apparatus. A tool assembly is disposed on the distal end of the shaft. The tool assembly includes a first jaw member supporting a cartridge assembly having a plurality of fasteners and a sled positioned to eject the fasteners from the cartridge assembly and a second jaw member supporting an anvil. The first jaw member is movable in relation to the second jaw member between spaced and approximated positions. A sled pusher assembly includes a sled pusher having a distal end configured to engage the sled of the cartridge assembly. A drive beam assembly includes a latch assembly having a latch releasably coupled to the sled pusher assembly. Distal translation of the drive beam assembly from a refracted position towards an advanced position effects movement of the first and second jaw members to the approximated position and disengages the latch of the latch assembly from the sled pusher assembly to facilitate distal movement of the sled pusher independently of the drive beam assembly. Distal movement of the sled pusher independently of the drive beam assembly also advances the distal end of the sled pusher into engagement with the sled of the cartridge assembly to eject the plurality of fasteners from the cartridge assembly.

BRIEF DESCRIPTION OF THE DRAWING

Various embodiments of the present disclosure are described hereinbelow with references to the drawings, wherein.

DETAILED DESCRIPTION

Figure 1A:
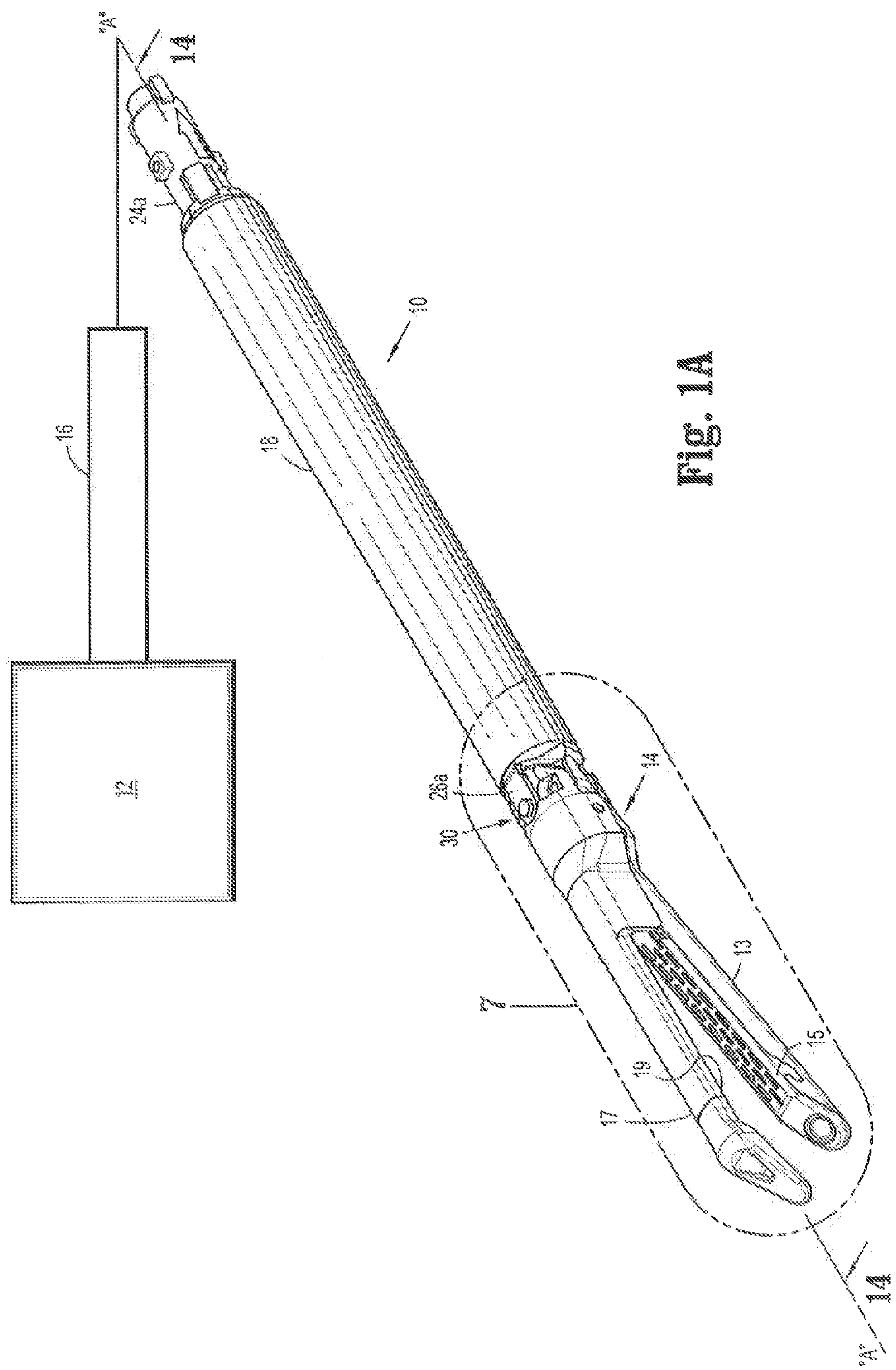
FIG. 1A is a perspective view of a reload according to an embodiment of the instant disclosure, the reload configured for use with a surgical apparatus that is shown schematically in FIG. 1A.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Referring initially to FIG. 1A, a reload 10 in accordance with the present disclosure is shown. The reload 10 may be configured to be coupled to a variety of different surgical actuating devices, shown schematically as 12 in FIG. 1A, including manually operated actuation devices, robotically controlled actuation devices, electromechanical actuation devices, motorized actuation devices, etc. The surgical actuating device 12 includes a shaft assembly 16 having a distal end configured to releasably support the reload 10.

Figure 1B:
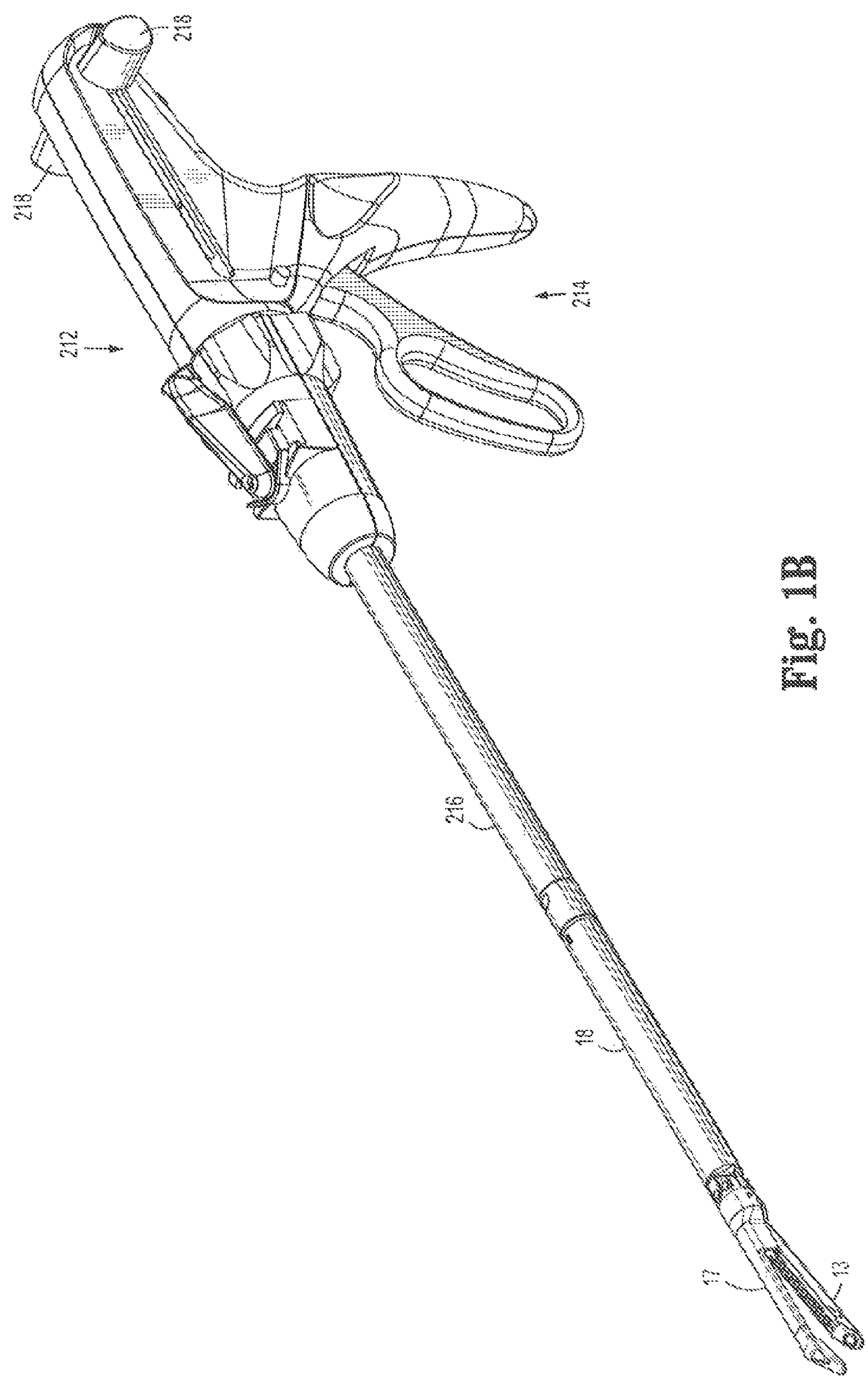
FIG. 1B is a perspective view of one type of surgical stapler that may be utilized with the reload shown in FIG. 1A.

In one embodiment illustrated in FIG. 1B, the surgical actuating device 12 is a manually operated stapler 212 which includes a handle assembly 214 and a shaft assembly 216 that engages and supports the reload 10. The handle assembly 214 includes a pair of retraction knobs 218 that is configured to return the stapler 212 to a retracted configuration. For a more detailed description of the operation and the operative components of the stapler 212, reference is made to commonly-owned U.S. Pat. No. 5,865,361 to Milliman, the entire contents of which are hereby incorporated by reference.

Figure 2:
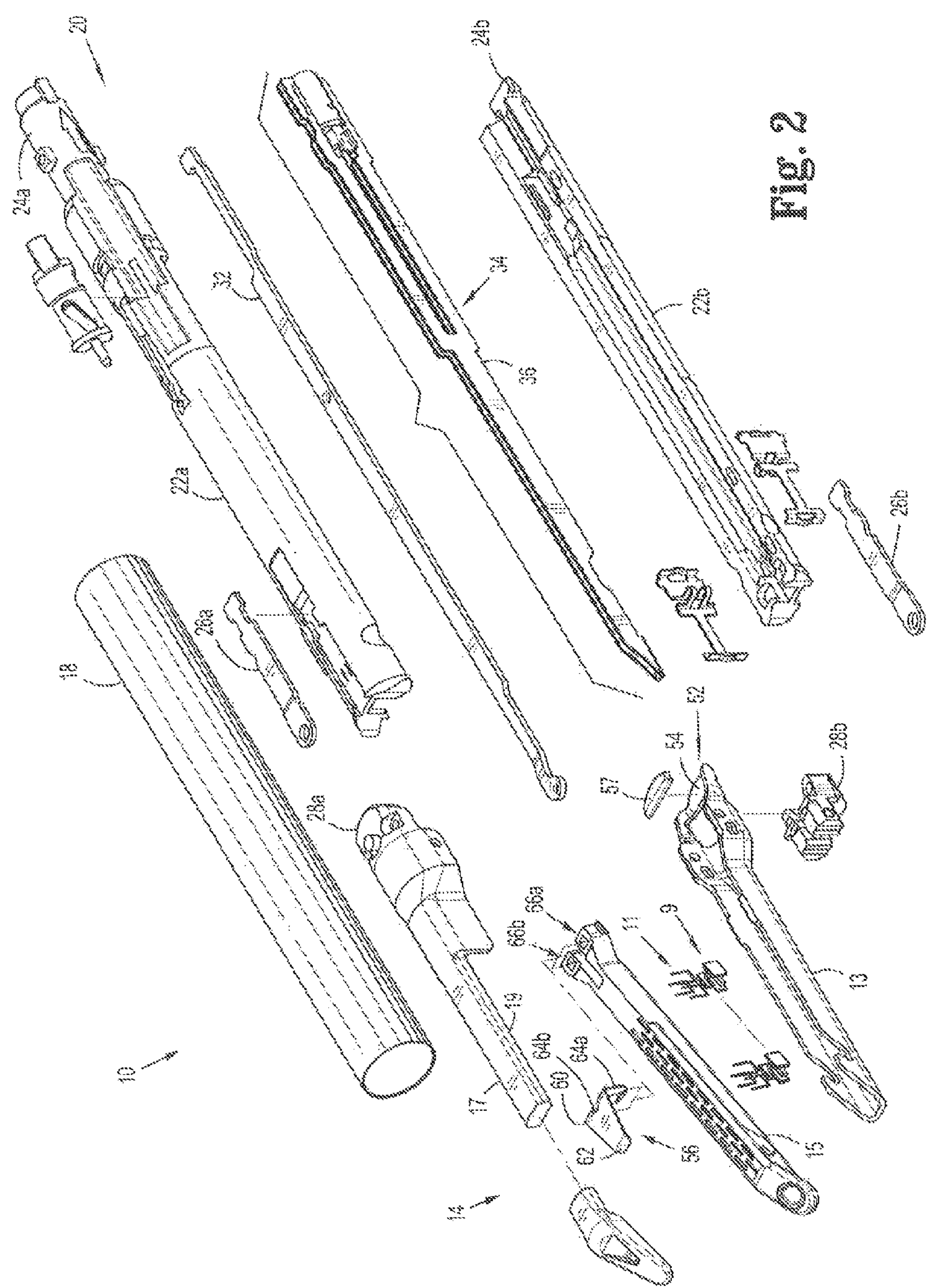
FIG. 2 is an exploded view of the reload shown in FIG. 1A with parts separated.

FIG. 2 is a perspective view of the reload 10 with parts separated. The reload 10 includes an outer tube 18 that houses a shaft assembly 20 configured to couple the reload 10 to the shaft assembly 16 of the actuating device 12 (see FIG. 1A). The shaft assembly 20 includes an upper housing portion 22*a* and lower housing portion 22*b* that, when coupled to one another, house components of the reload 10. Proximal ends 24*a*, 24*b* of the upper and lower housing portions 22*a*, 22*b* are configured to releasably couple with the distal end of the shaft assembly 16 of the actuating device 12 (e.g., see the '361 patent). A distal end of the housing portions 22*a*, 22*b* of the shaft assembly 20 supports upper and lower coupling members 26*a*, 26*b* respectively. A distal end of each of coupling members 26*a*, 26*b* is configured to pivotally engage upper and lower pivot portions 28*a*, 28*b*, respectively, of a pivot assembly 30 (see FIG. 1A). An articulating link 32 is slidably positioned within the upper and lower housing portions 22*a*, 22*b* and is configured to articulate an end effector or tool assembly 14 of the reload 10 in relation to the shaft assembly 20.

The tool assembly 14 includes a first jaw member 13 that supports a cartridge 15 and a second jaw member 17 that supports an anvil 19. The first jaw member 13 is pivotally supported in relation to the second jaw member 17 between spaced and approximated positions. The cartridge 15 houses a plurality of pushers 9 and fasteners 11. A dissecting tip 19*a* may be secured to a distal end of the anvil 19 to facilitate positioning of the anvil 19 in relation to tissue to be stapled. Such a dissecting tip 19*a* is described in U.S. Pat. No. 8,348,123 which is hereby incorporated herein by reference.

Referring also to FIGS. 3-6, the shaft assembly 20 includes a firing cam bar assembly 34 that is releasably engaged with a central rod (not shown) of the actuating device 12. The firing cam bar assembly 34 is configured to move the cartridge 15 from the spaced position (FIG. 1B) towards the anvil 19 to the approximated position (FIG. 18) as the firing cam bar assembly 34 is translated distally through the tool assembly 14. A distal end of the firing cam bar assembly 34 is also configured to push the plurality of pushers 9 to fire the plurality of fasteners 11 from the cartridge 15 as the firing cam bar assembly 34 is translated through the cartridge 15 as will be described in further detail below.

Figures 3, 4, 5:
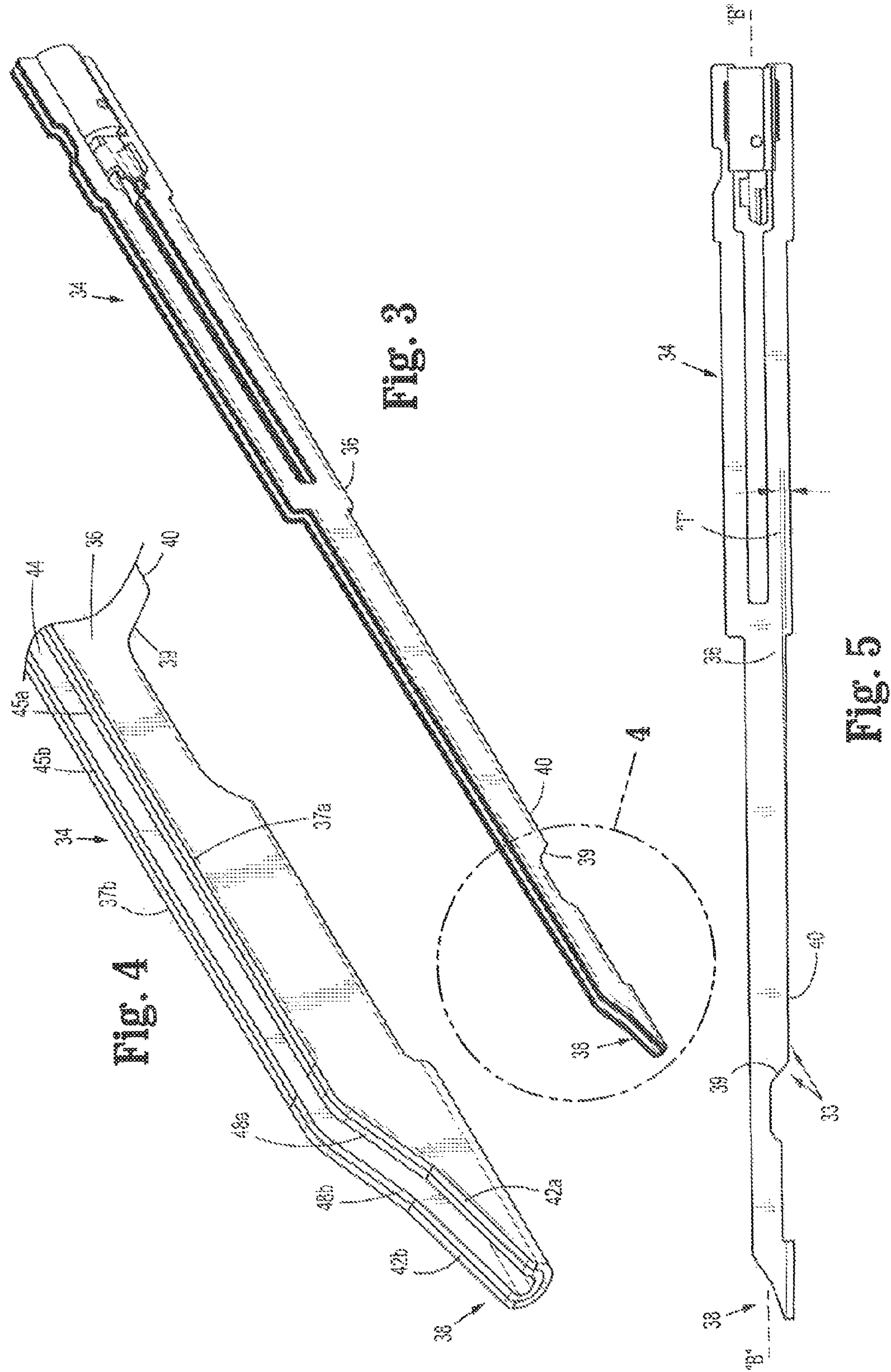
FIG. 3 is a perspective view of a firing cam bar assembly of the reload shown in FIGS. 1 and 2.
FIG. 4 is the indicated area of detail shown in FIG. 3.
FIG. 5 is a side view of the firing cam bar assembly shown in FIG. 3.

The firing cam bar assembly 34 includes a first firing cam bar 36 having an elongated configuration defined by left and right sidewalls 37*a*, 37*b*, which have a distal end 38. Each of the left and right sidewalls 37*a* and 37*b* of the cam bar 36 includes a cam surface 33 having a first cam portion 39 and a second cam portion 40. Each of the first cam portions 39 is disposed distally and at an angle in relation to one of the second cam portions 40 which is defined along a bottom/lower surface of the left and right sidewalls 37*a*, 37*b*. Only one of the second cam portions 40 can be seen in FIGS. 3-5. The configuration of the first cam portions 39 of the cam surface 33 facilitates movement of the first jaw member 13 towards the second jaw member 17 from the spaced position to the approximated position so that tissue may be clamped as will be described in further detail below. The second cam portions 40 are elongated in comparison to the first cam portions 39 and taper inwardly a distance "T" (FIG. 5) in relation to a longitudinal axis "B-B" of the firing cam bar assembly 34 toward a proximal end of the firing cam bar assembly 34 (FIG. 5). The taper "T" controls a tissue gap distance between the first and second jaw members 13, 17 when the first and second jaw members 13, 17 are moved toward the approximated position, as will be described in further detail below.

Figure 19:
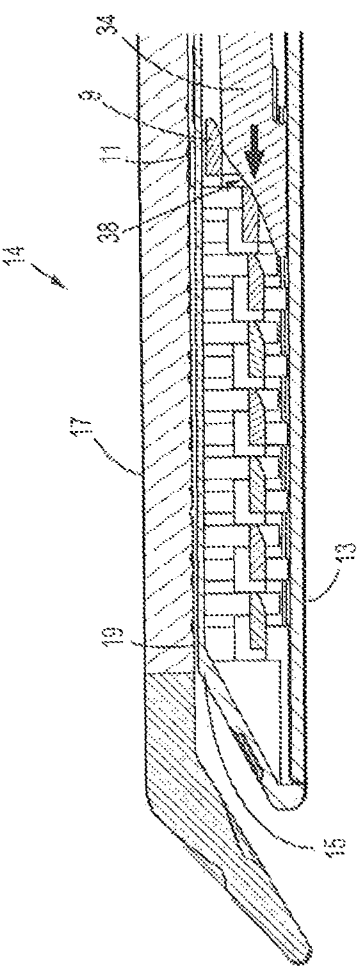
FIG. 19 is a partial, cross sectional view of the distal end of the reload shown in FIG. 15 illustrating a pusher contacting surface of the firing cam bar assembly pushing a pusher of the cartridge as the firing cam bar assembly is being translated through the cartridge to fire fasteners of the cartridge.

The distal end 38 of the first firing cam bar 36 includes two pusher contacting surfaces 42*a*, 42*b* (FIGS. 4 and 6) which are aligned with the plurality of pushers 9 of the cartridge 15 (FIG. 19). The pusher contacting surfaces 42*a*, 42*b* are configured to contact the plurality of pushers 9 to deploy the plurality of surgical fasteners 11 from the cartridge 15.

Figure 6:
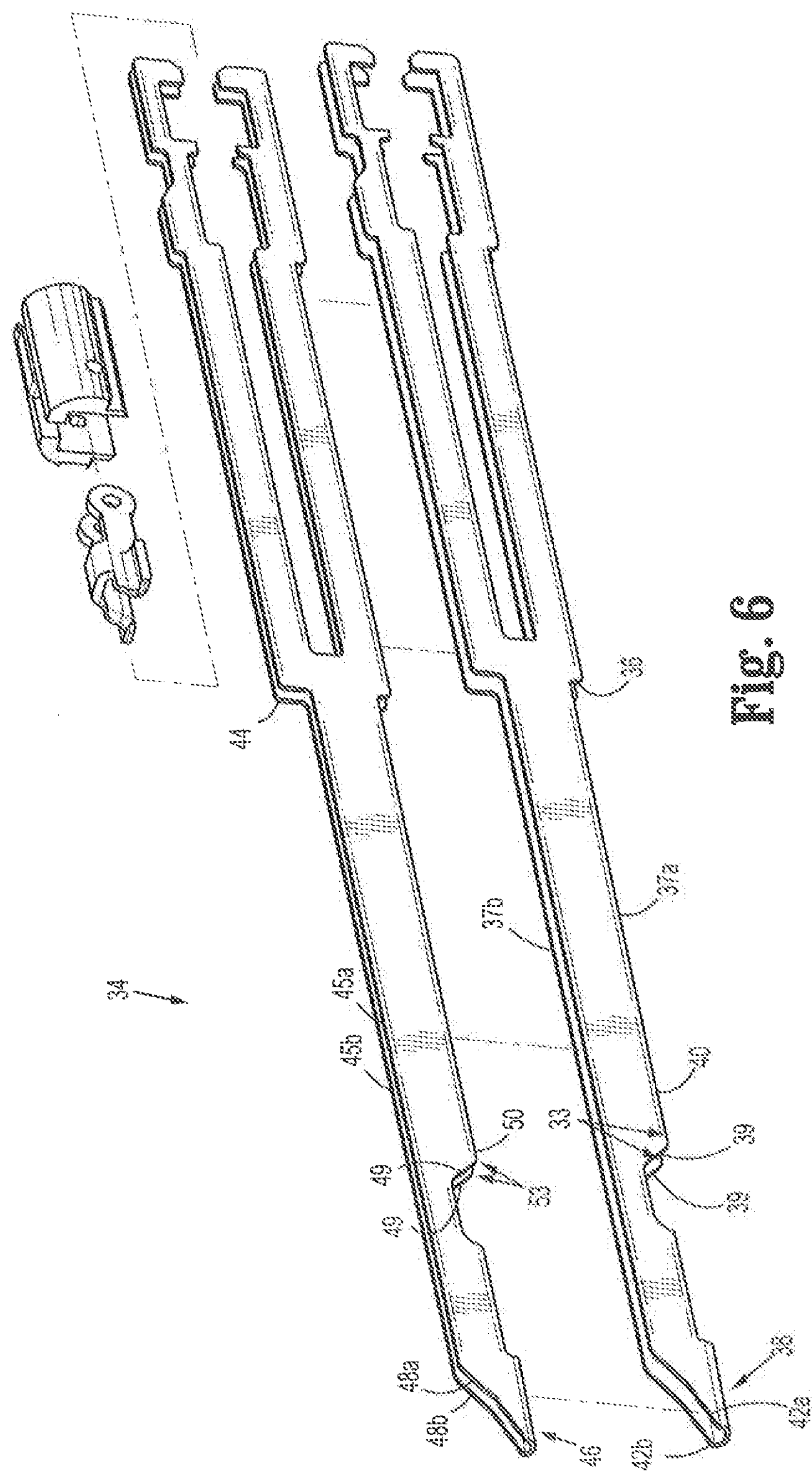
FIG. 6 is an exploded view of the firing cam bar assembly shown in FIG. 3 with parts separated.
Figure 7:
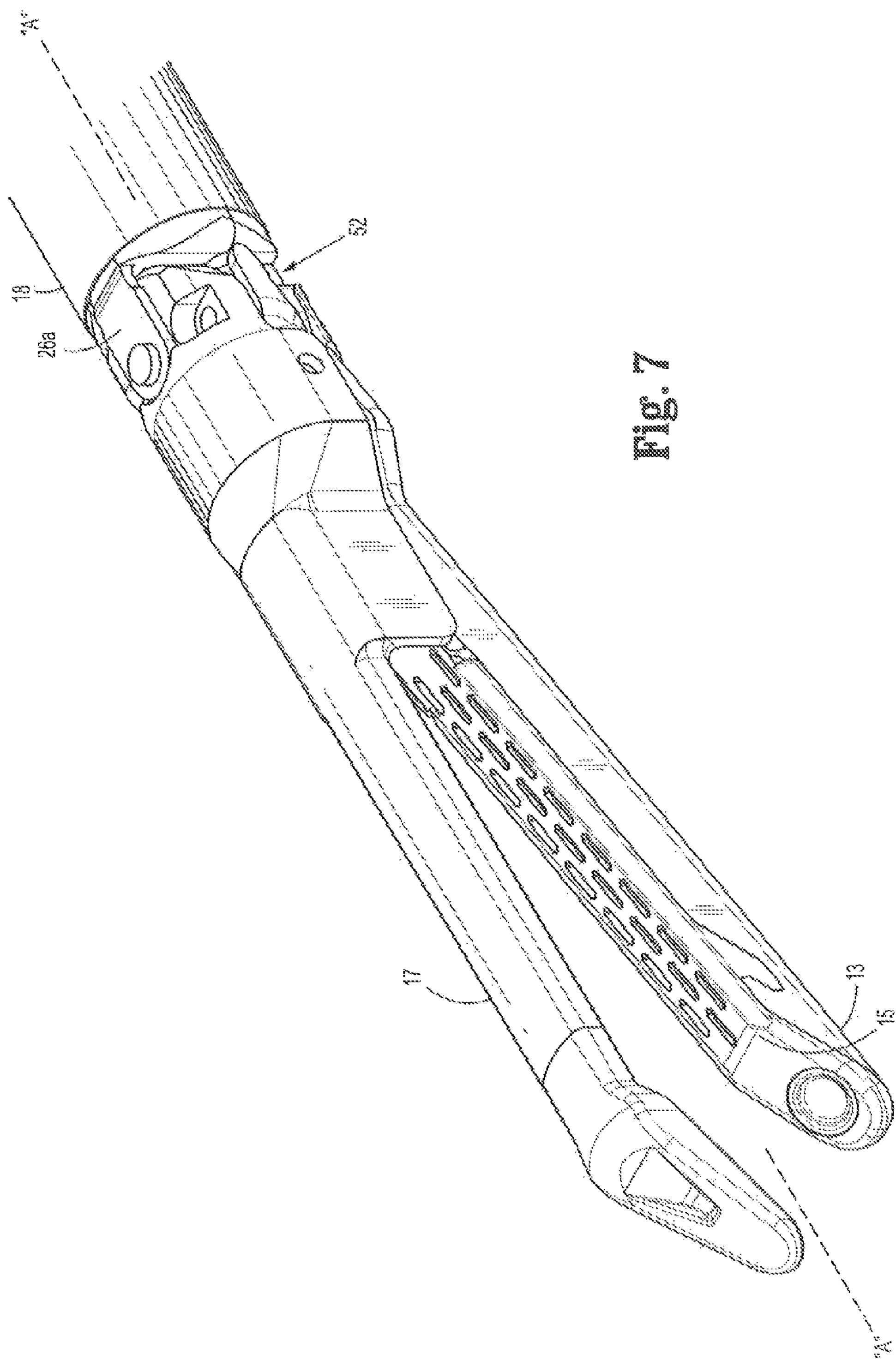
FIG. 7 is the indicated area of detail shown in FIG. 1A.

In the illustrated embodiment, the firing cam bar assembly 34 includes a second or inner firing cam bar 44 that is similar to the first firing cam bar 36. The first and second firing cam bars 36, 44 form a nested configuration with one another (as best shown in FIG. 6). The second firing cam bar 44 has an elongated configuration defined by left and right sidewalls 45*a*, 45*b*, which have a distal end 46. Each of the left and right sidewalls 45*a* and 45*b* of the cam bar 44 includes a cam surface 53 having a first cam portion 49 and second cam portion 50. The first cam portions 49 of the cam surface 53 are disposed distally and at an angle in relation to the second cam portions 50 (only one of the second portions 50 is shown) of the cam surface 53. The distal end 46 of the second firing cam bar 44 includes two pusher contacting surfaces 48*a*, 48*b* which are aligned with the plurality of pushers 9 of the cartridge 15 to contact the plurality of pushers 9 to deploy the plurality of surgical fasteners 11 from the cartridge 15 (FIG. 19).

The first and second firing cam bars 36, 44 may be formed from any suitable material including, but not limited to, plastic, metal, etc. In embodiments, the first and second firing cam bars 36, 44 are formed from metal.

While the firing cam bar assembly 34 has been described herein as including first and second firing cam bars 36, 44, greater or fewer firing cam bars may be utilized. For example, in embodiments, the second firing cam bar 44 may be omitted. In this particular embodiment, the configuration of the first firing cam bar 36 of the firing cam bar assembly 34 may be modified to include features of the second firing cam bar 44. For example, the left and right sidewalls 37*a*, 37*b* of the first firing cam bar 36 may be widened at the distal end 38 to align with all of the rows of the plurality of pushers 9 for ejecting all of the plurality of fasteners 11 disposed within the cartridge 15. Alternately, the second firing cam bar 44 can be omitted with no change to the configuration of the first firing cam bar 36.

Referring to FIGS. 7-13, a cantilever 52 (FIG. 13) is provided at a proximal end of the first jaw member 13. The cantilever 52 may be monolithically formed with the first jaw member 13. Alternatively, the cantilever 52 may be formed as a separate component apart from the first jaw member 13 and coupled to the first jaw member 13 via one or more suitable coupling methods, e.g., welding. The cantilever 52 is disposed adjacent the pivot assembly 30 between the lower coupling member 26*b* and a distal end of the articulating link 32 (see FIG. 9 for example).

Figure 13:
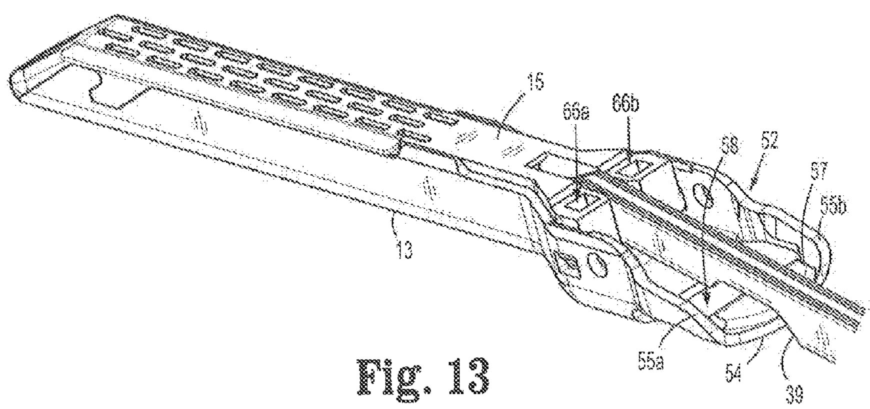
FIG. 13 is the indicated area of detail shown in FIG. 12.

In the illustrated embodiment, the cantilever 52 is in the form of a bridge 54 that is formed between side projections 55*a*, 55*b* that extend proximally from the proximal end of the first jaw member 13 (FIG. 13). The bridge 54 is disposed transverse to a longitudinal axis "A-A" (FIG. 7) defined through the shaft assembly 20 of the reload 10.

The bridge 54 supports a cam member 57 (FIGS. 2 and 13) which is positioned to be slidably engaged by the first and second cam portions 39, 49 and 40, 50, respectively, of the first and second firing cam bars 36, 44 when the firing cam bar assembly 34 is advanced distally within the cartridge 15, as will be described in greater detail below. The cam member 57 may be slanted (as shown in the illustrated embodiment) or otherwise configured to operate in conjunction with the taper "T" of the second cam portions 40, 50 of the first and second cam bars 36, 44, respectively, to control the size of the tissue gap between the first and second jaw members 13, 17 when the first and second jaw members 13, 17 are in the approximated configuration. The cam member 57 may be coupled to the bridge 54 via one or more suitable coupling methods, e.g., adhesive, welding, etc. Alternatively, the cam member 57 may be omitted and the bridge 54 may be integrally formed with a cam surface configured to control the size of the tissue gap. In accordance with the instant disclosure, the bridge 54 engages the firing cam bars 36, 44 to close the first and second jaw members 13, 17 in both the linear and articulated positions.

Figures 8, 9:
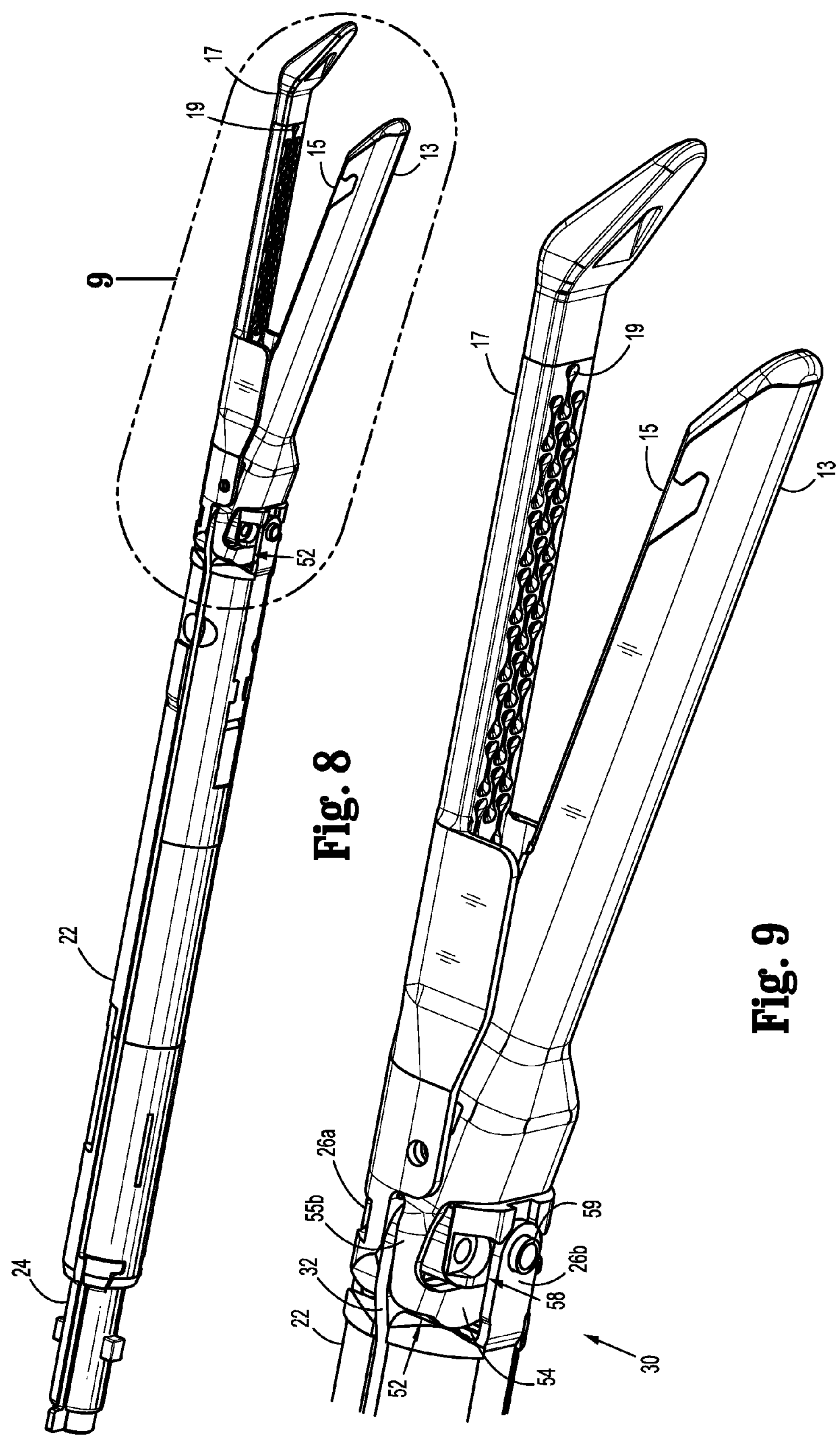
FIG. 8 is a perspective view of the reload shown in FIG. 1A with an outer tube of the reload removed.
FIG. 9 is the indicated area of detail shown in FIG. 8.
Figures 10, 11:
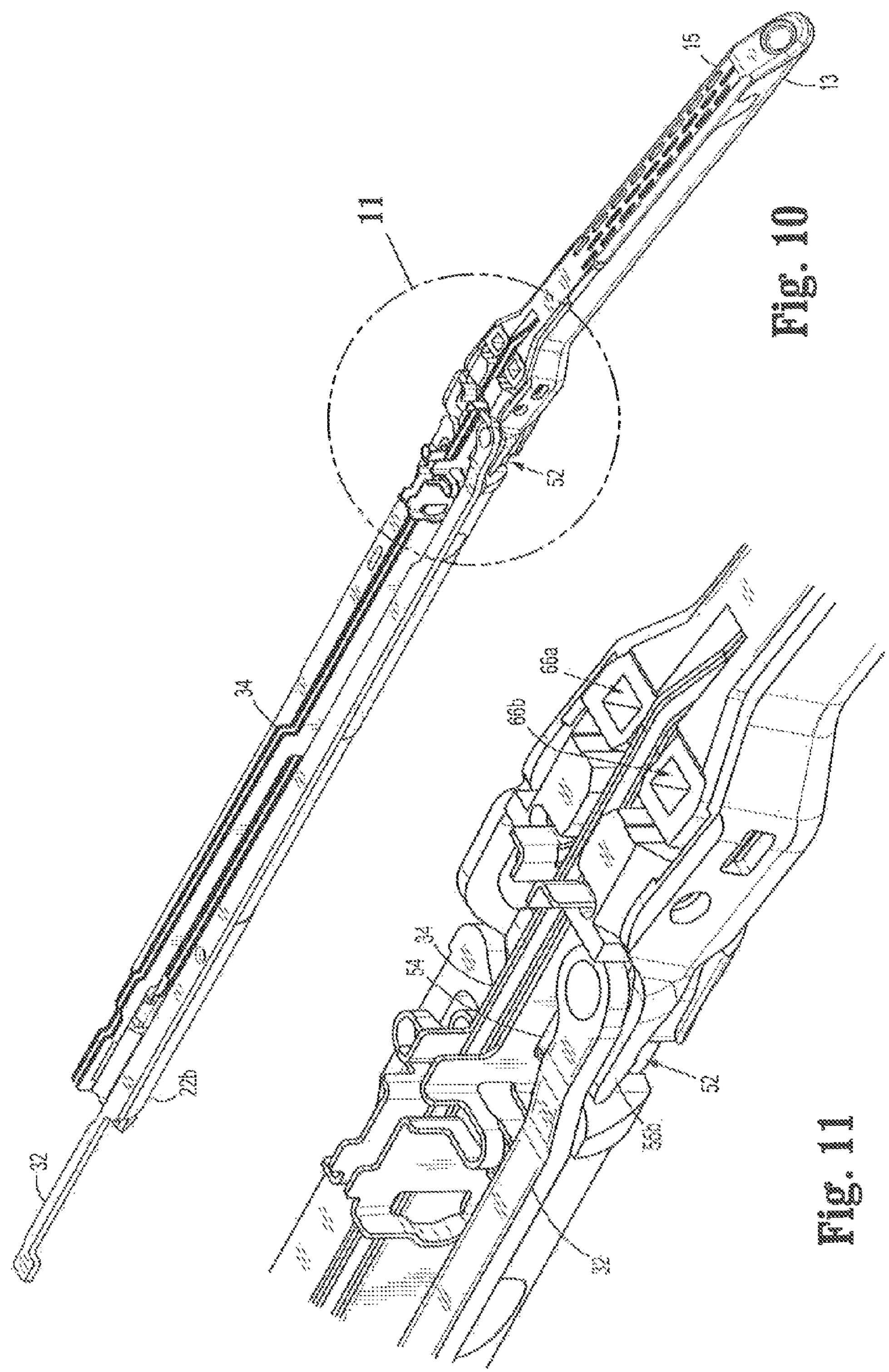
FIG. 10 is a perspective view of the reload shown in FIG. 1A with parts removed illustrating the firing cam bar assembly coupled to a cartridge of a tool assembly of the reload.
FIG. 11 is the indicated area of detail shown in FIG. 10.
Figure 12:
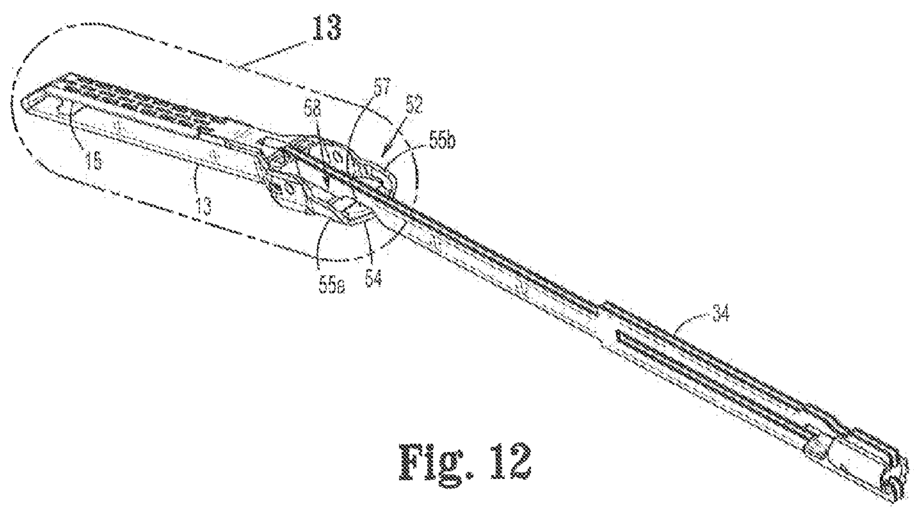
FIG. 12 is a perspective view of the reload shown in FIG. 1A with parts removed illustrating a cantilever of the cartridge in contact with the firing cam bar assembly.

Referring to FIG. 9, the cantilever 52 defines an aperture 58 between the side projections 55*a*, 55*b* and the bridge 54. The aperture 58 receives a rivet 59 (FIG. 9) for coupling the lower coupling member 26*b* to the lower portion 28*b* of the pivot assembly 30 during manufacture of the reload 10.

Figure 14:
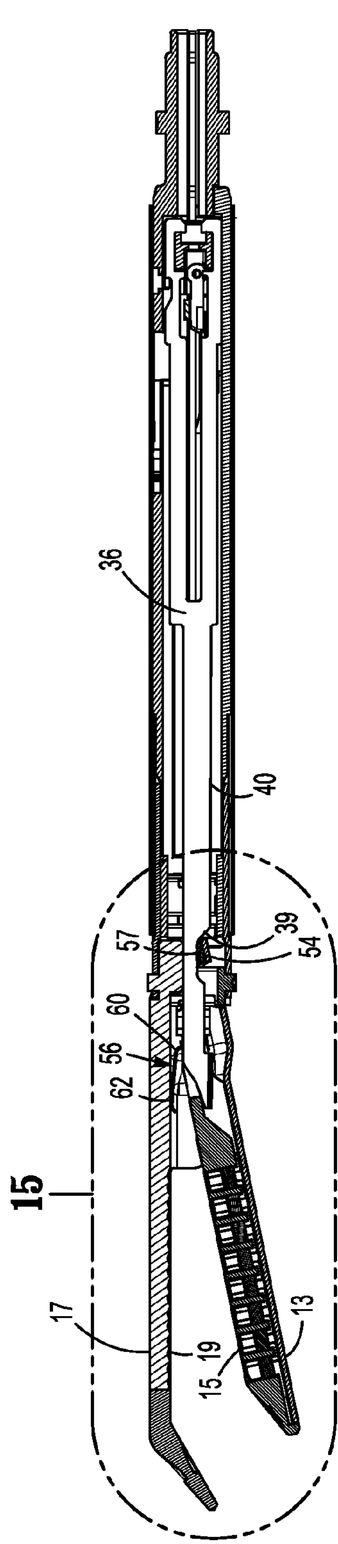
FIG. 14 is a cross sectional view taken along section line 14-14 in FIG. 1A.
Figure 15:
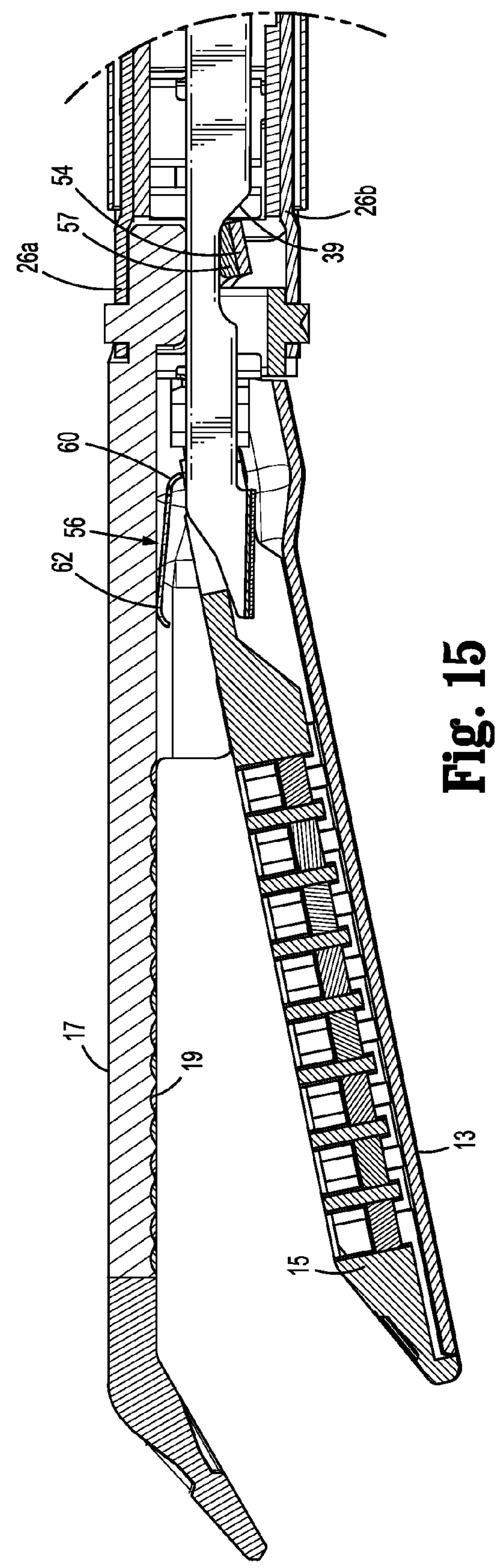
FIG. 15 is the indicated area of detail shown in FIG. 14.

Referring to FIGS. 2, 14, and 15, a resilient member 56 is provided on the cartridge 15 and is positioned to bias the cartridge 15 radially away from the anvil 19 towards the spaced position. The resilient member 56 includes a proximal end 60 that is coupled to a proximal end of the cartridge 15 and a distal end 62 that is positioned to contact at least a portion of the anvil 19. In the illustrated embodiment, the proximal end 60 of the resilient member 56 includes two finger portions 64*a*, 64*b* that seat within two corresponding apertures 66*a*, 66*b* of suitable configuration defined at the proximal end of the cartridge 15 (see FIG. 2 and FIG. 13).

Figure 16:
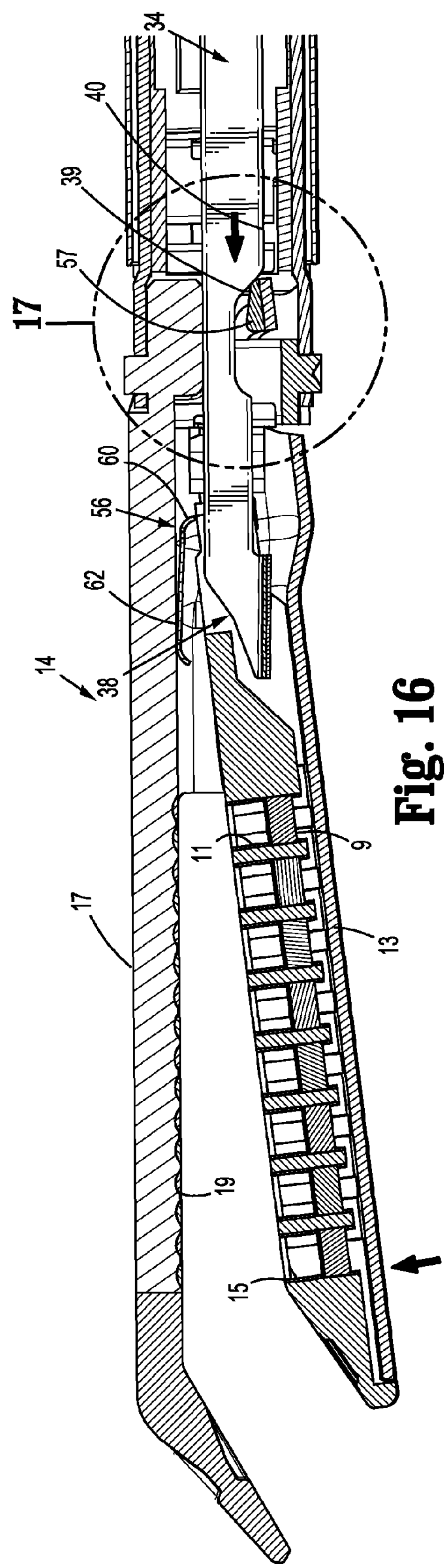
FIG. 16 is a partial, cross sectional view of a distal end of the reload shown in FIG. 1A illustrating the firing cam bar assembly being translated through the cartridge to fire fasteners of the cartridge.
Figure 17:
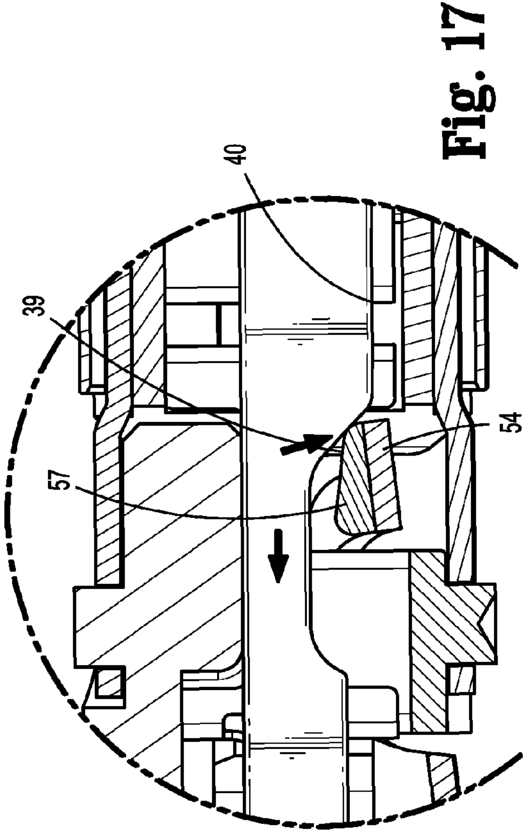
FIG. 17 is the indicated area of detail shown in FIG. 16.

Referring to FIGS. 16 and 17, in use, prior to positioning tissue between the first and second jaw members 13, 17, the tool assembly 14 is in the spaced or unapproximated position. In this position, the distal ends 38, 46 of the first and second firing cam bars 36, 44 are positioned proximally of the plurality of pushers 9 and the plurality of fasteners 11. In addition, in this configuration an engagement portion of the first cam portions 39, 49 (see also FIG. 6) of the first and second firing cam bars 36, 44 is positioned proximally of the cam member 57. As discussed above, the resilient member 56 is positioned to urge the jaw member 13 to the spaced or unapproximated position.

Figure 18:
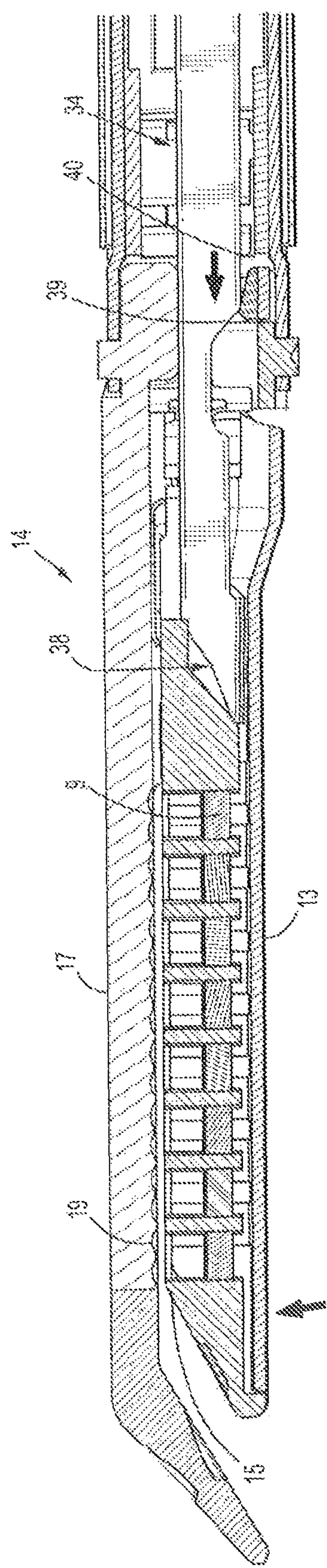
FIG. 18 is a partial, cross sectional view of the distal end of the reload shown in FIG. 15 illustrating a cam surface of the firing cam bar assembly sliding along the cantilever of the cartridge as the firing cam bar assembly is being translated through the cartridge to fire fasteners of the cartridge.

Referring to FIG. 18, when the firing cam bar assembly 34 is advanced distally, the first cam portions 39, 49 of the first and second firing cam bars 36, 44 and engage the cam member 57 of the bridge 54 and pivot the first jaw member 13 including the cartridge 15 towards the anvil 19 of the second jaw member 17 to move the jaw member 13 including the cartridge 15 to the clamped or approximated configuration. In this example, the cartridge is pivotably attached to the second jaw member. However, any of the embodiments disclosed herein can have a first jaw member, or second jaw member, or both that are pivotably movable.

Figure 20:
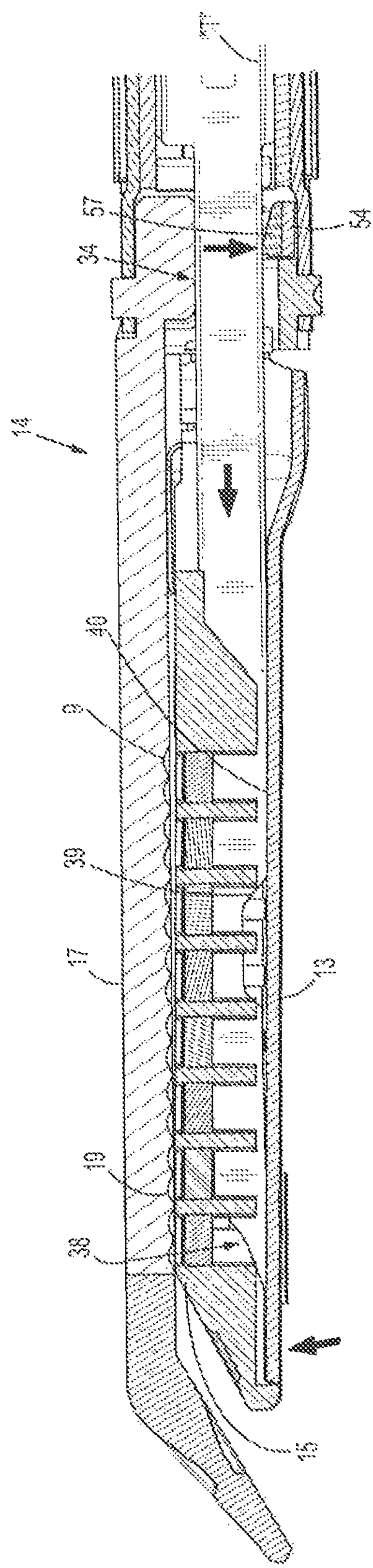
FIG. 20 is a partial, cross sectional view of the distal end of the reload shown in FIG. 15 illustrating the cam surface of the firing cam bar assembly and the cantilever of the cartridge in contact with one another to maintain a specific tissue gap distance between the cartridge and an anvil of the tool assembly.
Figure 21:
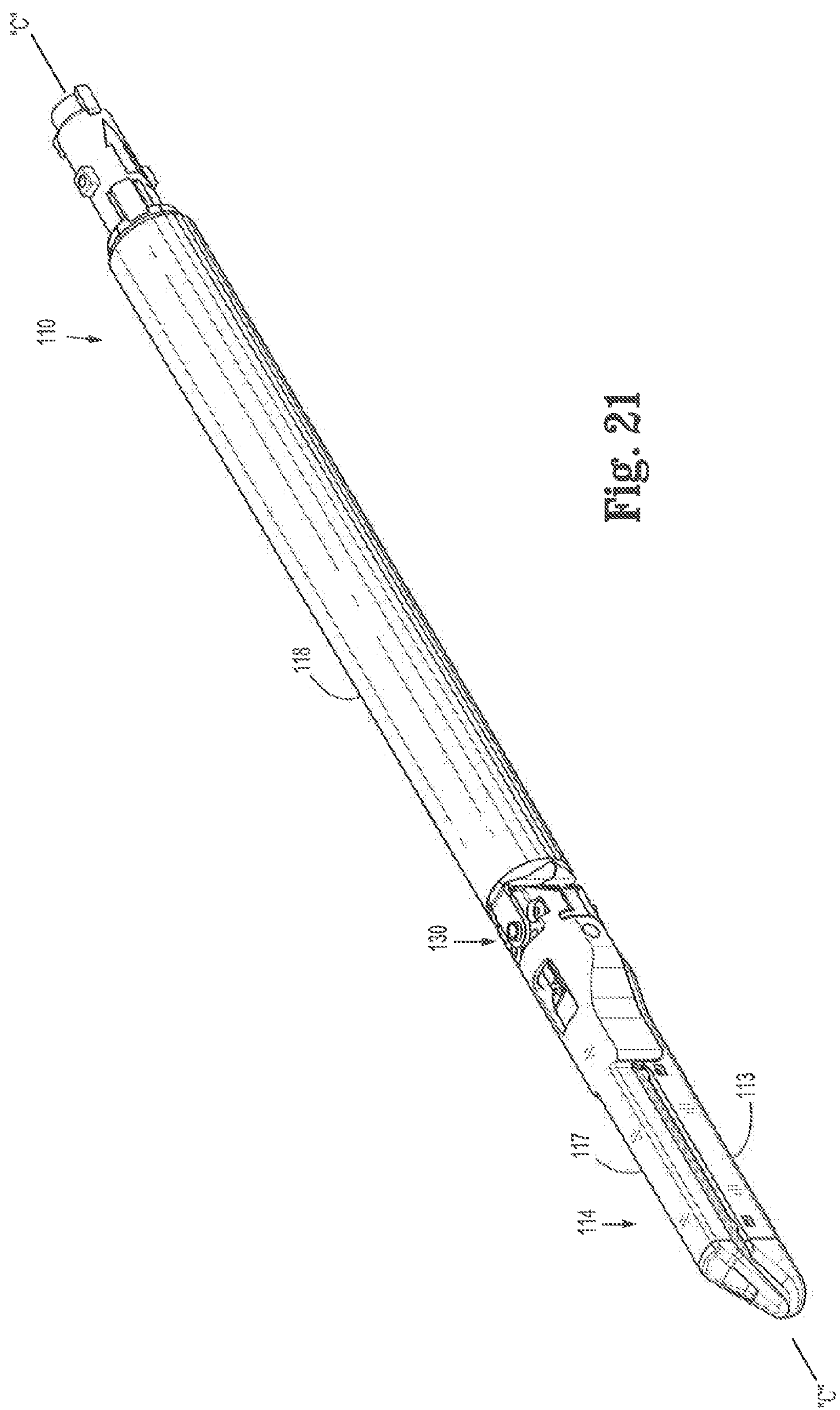
FIG. 21 is a perspective view of a reload according to another embodiment of the instant disclosure, the reload configured for use with the surgical apparatus that is shown schematically in FIG. 1A.

Referring to FIG. 19, continued distal translation of the firing cam bar assembly 34 moves the distal ends 36, 48 of the first and second firing cam bars 36, 44 into contact with the plurality of pushers 9 sequentially to eject the plurality of fasteners 11 from the cartridge 15 and into the anvil 19 to staple clamped tissue. In accordance with the present disclosure, as the firing cam bar assembly 34 is translated through the cartridge 15, engagement of the cam member 57 on the bridge 54 with the taper "T" (FIG. 15) on the second cam portions 40, 50 of the first and second firing cam bars 36, 44 controls the position of the jaw member 17 in relation to the jaw member 13 to selectively maintain a desired tissue gap distance between the first and second jaw members 13, 17 (FIG. 20). In accordance with the instant disclosure, the degree of the taper "T" on the second cam portions 40, 50 of the first and second firing cam bars 36, 44 may be uniform or non-uniform to selectively control the tissue gap distance during translation of the cam bar assembly 34 through the cartridge 15. It is noted that the taper "T" may define a positive or negative slope in the proximal direction to provide the proper or desired tissue gap distance.

The unique configuration of the jaw member 13 including the firing cam bar assembly 34 and cantilever 52 provides a simple design for approximating and controlling the tissue gap between the cartridge 15 and the anvil 19. Additionally, the presently disclosed tool assembly 14 allows for the tissue gap between the first and second jaw members 13, 17 to be accurately controlled by the second cam portions 40, 50 of the first and second firing cam bars 36, 44 as the firing cam bar assembly 34 is advanced.

In embodiments, the tool assembly 14 can be integrally formed with the surgical actuating device 12. In this particular embodiment, the tool assembly 14 can be operably coupled to an articulating assembly, e.g., the pivot assembly 30, which may be supported at a distal end of the shaft assembly 16 of the surgical actuating device 12. Alternatively, the pivot assembly 30 can be omitted and the tool assembly 14 can be directly connected to the distal end of the shaft assembly 16 of the surgical actuating device 12.

FIGS. 21-44 illustrate a reload 110 according to another embodiment of the instant disclosure. The reload 110 is configured for use with the stapler 212 that is shown in FIG. 1B. Only the features that are unique to the reload 110 are described herein.

Figure 22:
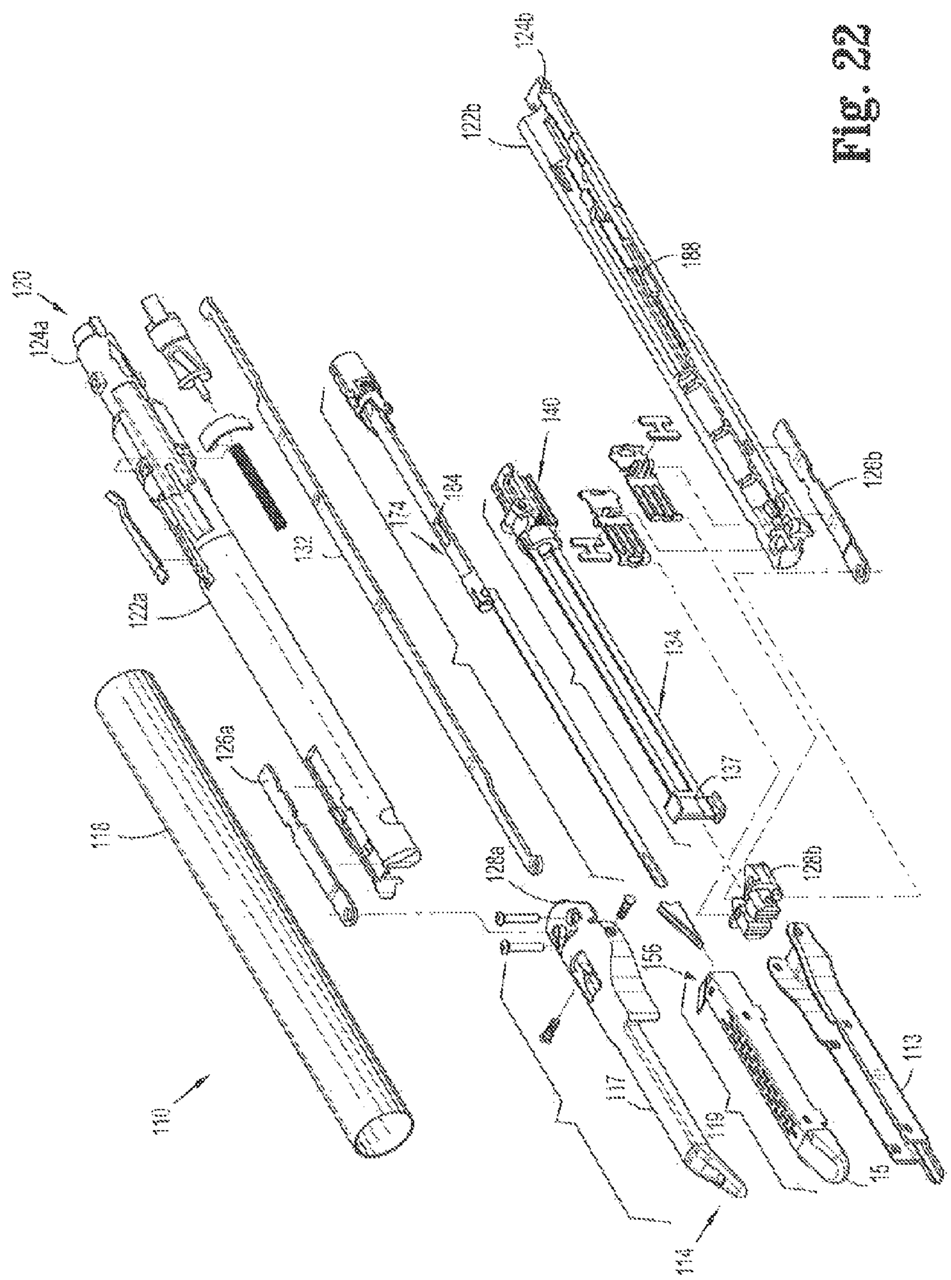
FIG. 22 is an exploded view of the reload shown in FIG. 21 with parts separated.

FIG. 22 is a perspective view of the reload 110 with parts separated. The reload includes an outer tube 118 that houses a shaft assembly 120 configured to couple the reload 110 with the shaft assembly 216 of the actuating device 212 shown in FIG. 1B. The shaft assembly 120 includes upper housing portion 122*a* and lower housing portion 122*b* that, when coupled to one another, house components of the reload 110. Proximal ends 124*a*, 124*b* of the upper and lower housing portions 122*a*, 122*b*, respectively, are configured to releasably couple to the distal end of the shaft assembly 216 of the actuating device 212 (see '361 patent for example). A distal end of the shaft assembly 120 includes a pair of upper and lower coupling members 126*a*, 126*b* that are configured to couple the shaft assembly 120 to the upper and lower pivot portions 128*a*, 128*b*, respectively, of a pivot assembly 130 (see FIG. 21). An articulating link 132 is slidably positioned within the upper and lower housing portions 122*a*, 122*b* and is configured to articulate an end effector or tool assembly 114 of the reload 110 relative to a longitudinal axis "C-C" (FIG. 21) defined through the shaft assembly 120.

Figure 23:
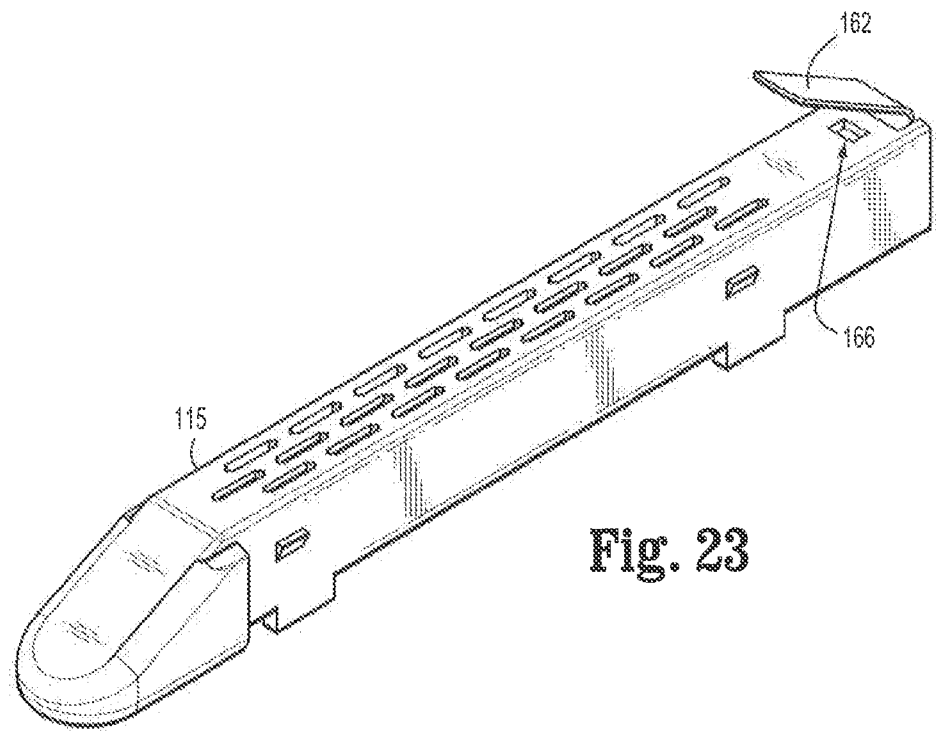
FIG. 23 is a perspective view of a cartridge assembly of the reload shown in FIG. 21.
Figure 24:
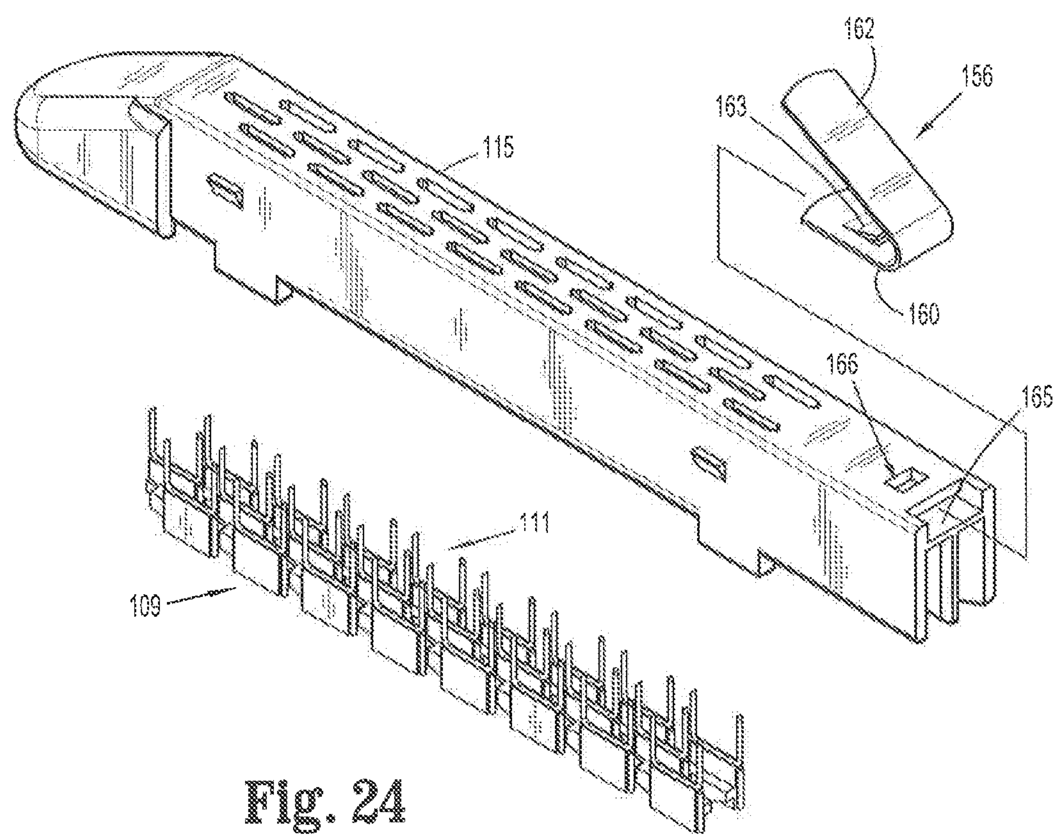
FIG. 24 is an exploded view of the cartridge assembly shown in FIG. 23 with parts separated.

Referring to FIGS. 22-24, the tool assembly 114 includes a first jaw member 113 that supports a cartridge 115 housing a plurality of pushers 109 and fasteners 111 and a second jaw member 117 that supports an anvil 119. The cartridge 115 supports a resilient member 156 which is positioned to bias the cartridge 115 radially away from the anvil 119 towards an unapproximated or spaced configuration. The resilient member 156 includes a base portion 160 (FIG. 24) that couples to a proximal end of the cartridge 115 and an upper portion 162 positioned to contact at least a portion of the anvil 119. The base portion 160 of the resilient member 156 is seated within a corresponding slot 165 defined at the proximal end of the cartridge 115 and includes one or more detents 163 (one detent 163 is shown in the figures) which is received in a corresponding indent 166 disposed on the cartridge 115 adjacent the slot 165 to couple the resilient member 156 to the cartridge 115.

Figure 25:
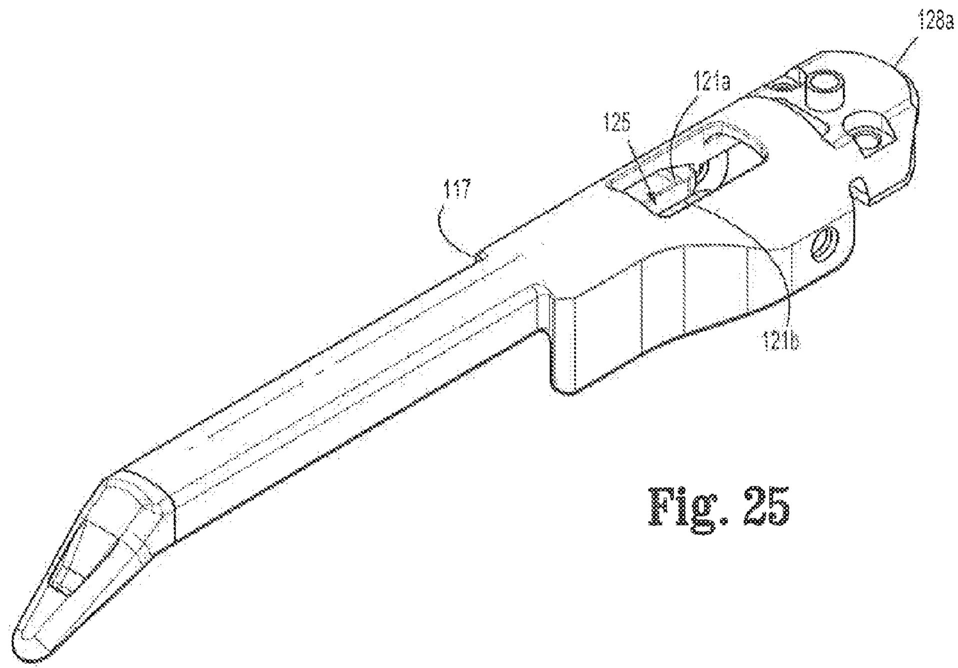
FIG. 25 is a perspective view of a second jaw member of the reload shown in FIG. 21.
Figure 26:
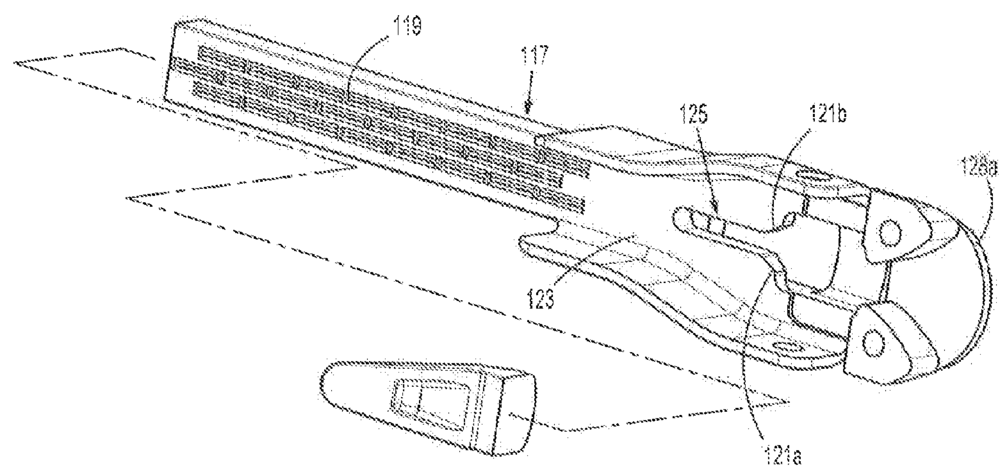
FIG. 26 is an exploded view of the second jaw member shown in FIG. 25 with parts separated.

Referring to FIGS. 25 and 26, the second jaw member 117 includes a pair of upper rails 121*a*, 121*b* that extend longitudinally along an interior wall portion 123 of the second jaw member 117. The upper rails 121*a*, 121*b* are separated by an elongated slot 125 which extends along the length of the upper rails 121*a*, 121*b*. The upper rails 121*a*, 121*b* are positioned along the interior wall portion 123 proximal to where the top portion 162 of the resilient member 156 contacts the interior wall portion 123 of the jaw member 117 (see FIG. 35 for example). A dissecting tip 157, such as disclosed in the '123 patent, may be secured to a distal end of the second jaw member 117 to facilitate positioning of the second jaw member 117 in relation to tissue to be stapled.

Figure 27:
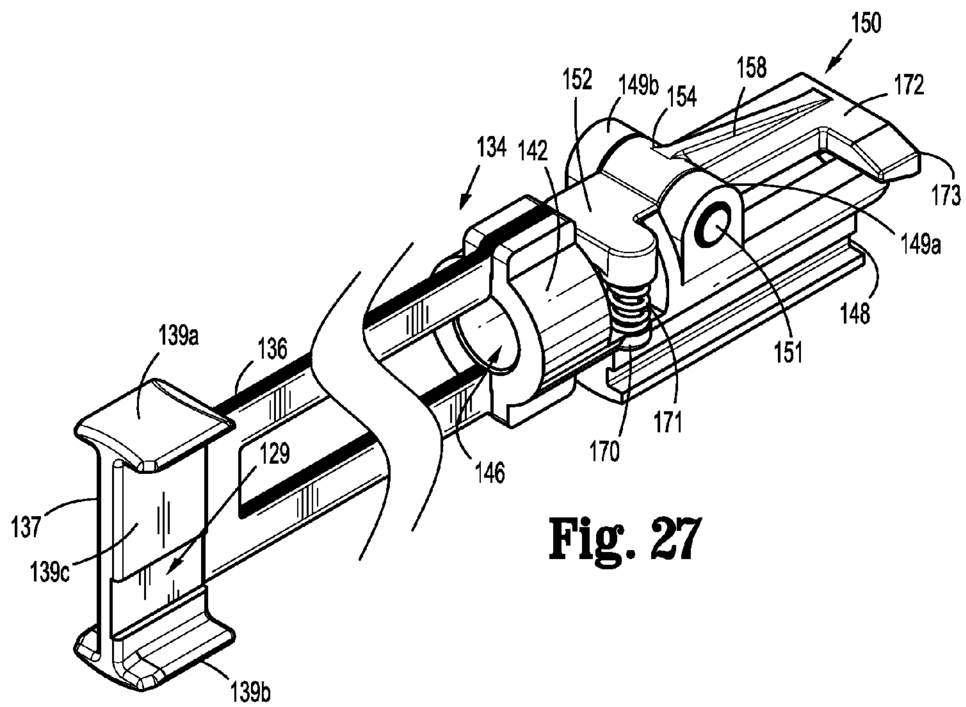
FIG. 27 is a perspective view of a drive beam assembly and latch assembly of the reload shown in FIG. 21.
Figure 28:
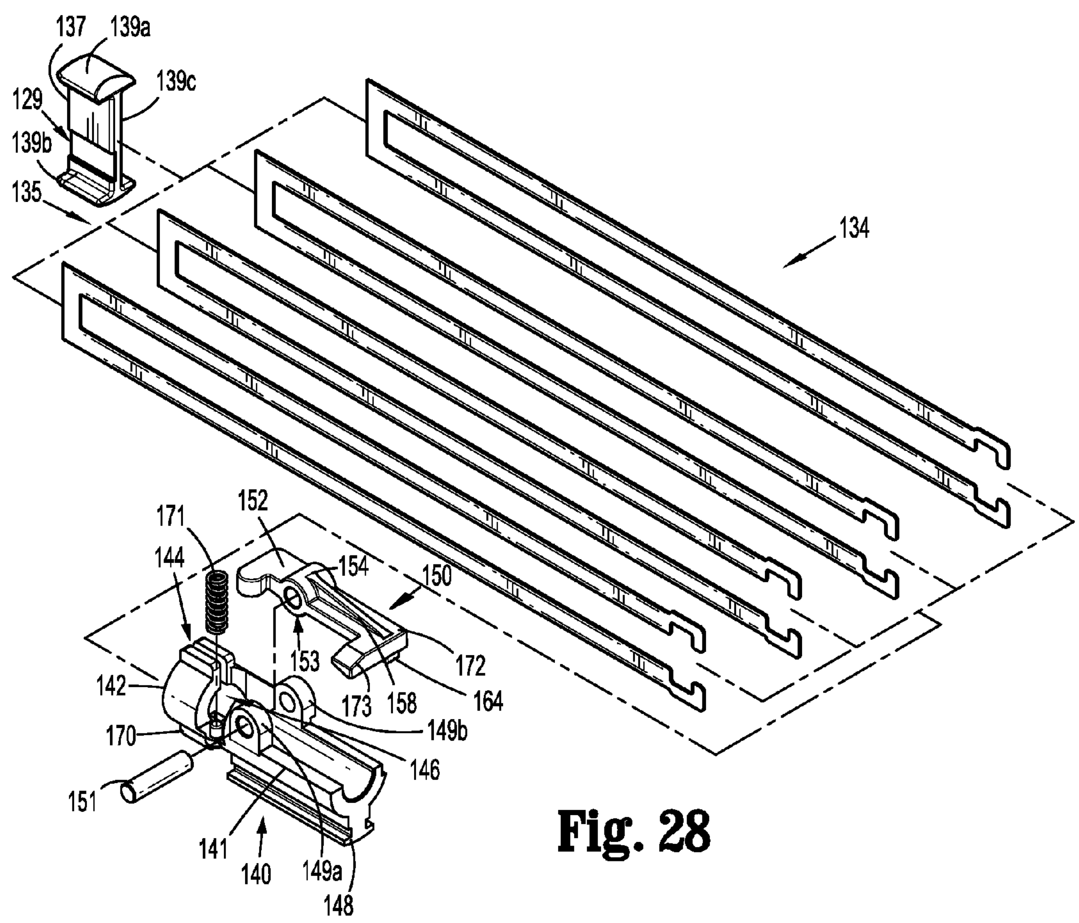
FIG. 28 is an exploded view of the drive beam and latch assembly shown in FIG. 27 with parts separated.

Referring also to FIGS. 27 and 28, the reload 110 (FIG. 21) includes a drive beam assembly 134 formed from a plurality of drive beam portions 135 that are coupled to one another to form a drive beam 136. A working end of the drive beam assembly 134 includes an I-beam 137 which is coupled to the distal end of the drive beam portions 135 and includes upper and lower flanges 139*a*, 139*b* respectively connected to each other by a strut 139*c*. Unlike conventional I-beams, the I-beam 137 does not include a knife or cutting blade at a leading edge of the strut 139*c*, as the I-beam 137 is not configured to sever stapled tissue. The I-beam 137 is translatable through the tool assembly 114 to approximate the first and second jaw members 113 and 117 and eject fasteners 111 from the cartridge 115 as will be described in further detail below. The upper flange 139*a* is positioned within the second jaw member 117 (FIG. 26) above the upper rails 121*a*, 121*b*. When the drive beam 136 of the drive beam assembly 134 is translated distally within the second jaw member 117, the upper flange 139 slides atop the upper flange 139*a* to prevent outward movement of the second jaw member 117 in relation to the first jaw member 113. Similarly, the strut 139*c* of the I-beam is positioned through an elongated slot 127 (see FIG. 31) that is defined through the first jaw member 113 such that the lower flange 139*b* is slidable along an exterior surface of the first jaw member 113 to prevent outward movement of the first jaw member 113 in relation to the second jaw member 117. A notch 129 is defined through a side wall of the strut 139*c*, the significance of which is described in greater detail below.

A latch assembly 140 is coupled to a proximal end of the drive beam assembly 134. The latch assembly 140 includes a latch body 141 including a collar 142 defining bottom and top slots 144 (only the top slot 144 is shown). The slots 144 are configured to receive a proximal end of the drive beam 136. A longitudinal aperture 146 of suitable configuration is defined through the collar 142 and is in general alignment with an elongated proximal portion 148 of the latch body 141. The latch body 141 of the latch assembly 140 includes a pair of opposing support members 149*a*, 149*b* which support a pivot pin 151. A protrusion 170 extends upwardly from the latch body of the latch assembly 140 adjacent the collar 142 and is configured to support a spring 171.

The latch assembly 140 includes a latch 150 having a generally elongated configuration including a distal portion 152, a medial portion 154 and a proximal portion 158. A transverse aperture 153 extends through the medial portion 154 and is configured to receive the pivot pin 151 for pivotally securing the latch 150 to the latch body 141 of the latch assembly 140. The distal portion 152 of the latch 150 is positioned to contact the spring 171 such that the spring 171 urges a proximal end 172 of the proximal portion 158 of the latch 150 downwardly towards the proximal portion 148 of the latch assembly 140 (as best shown in FIG. 27). A protrusion 164 is provided on a bottom surface and at the proximal end 172 of the proximal portion 158 of the latch assembly 150. A lateral offset extension 173 is also provided at the proximal end 172 of the latch assembly 150 and is configured to move the latch 150 upwardly against the bias of the spring 171, as will be described in greater detail below.

Figure 29:
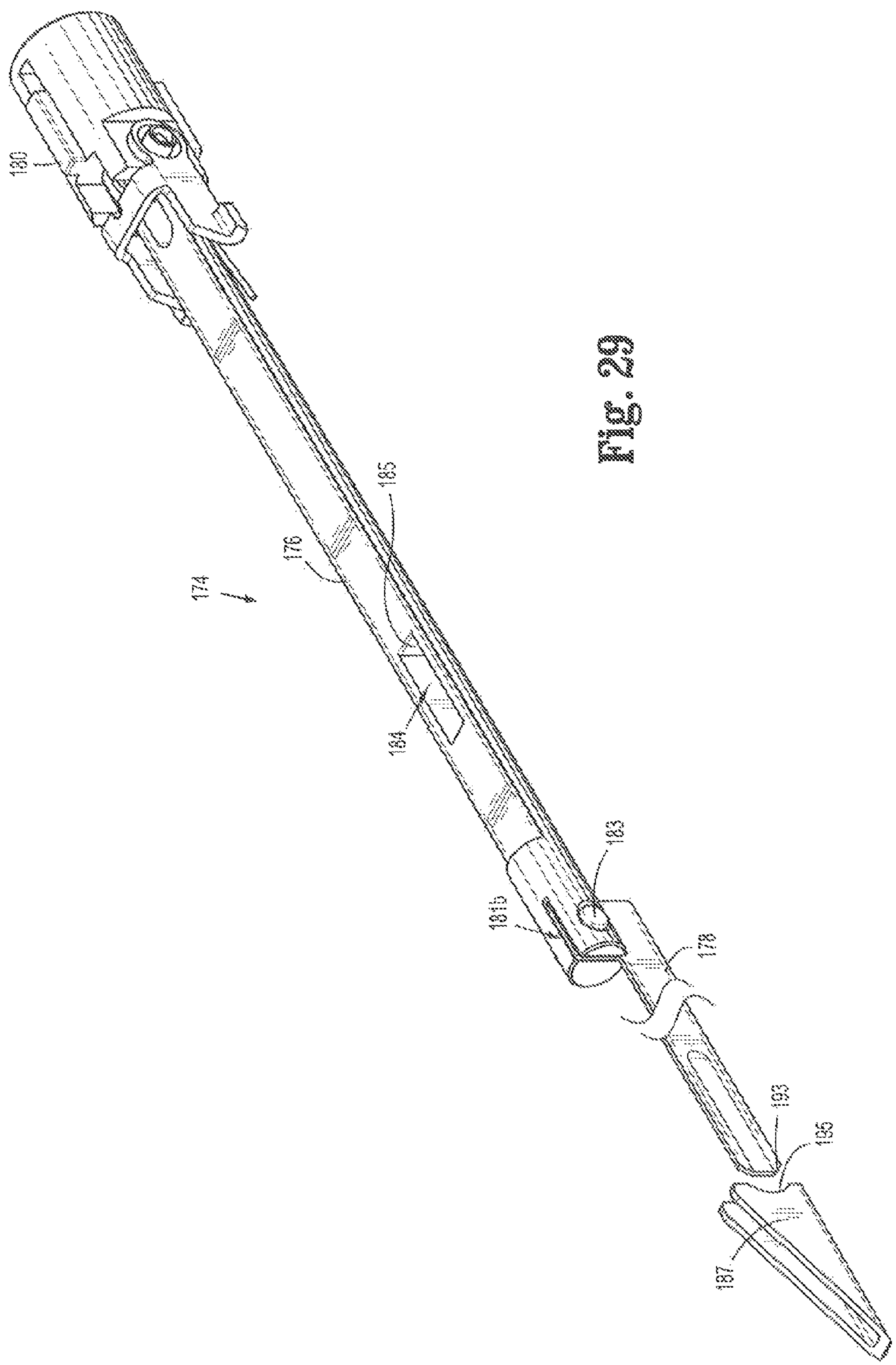
FIG. 29 is a perspective view of a sled pusher assembly of the reload shown in FIG. 21.
Figure 30:
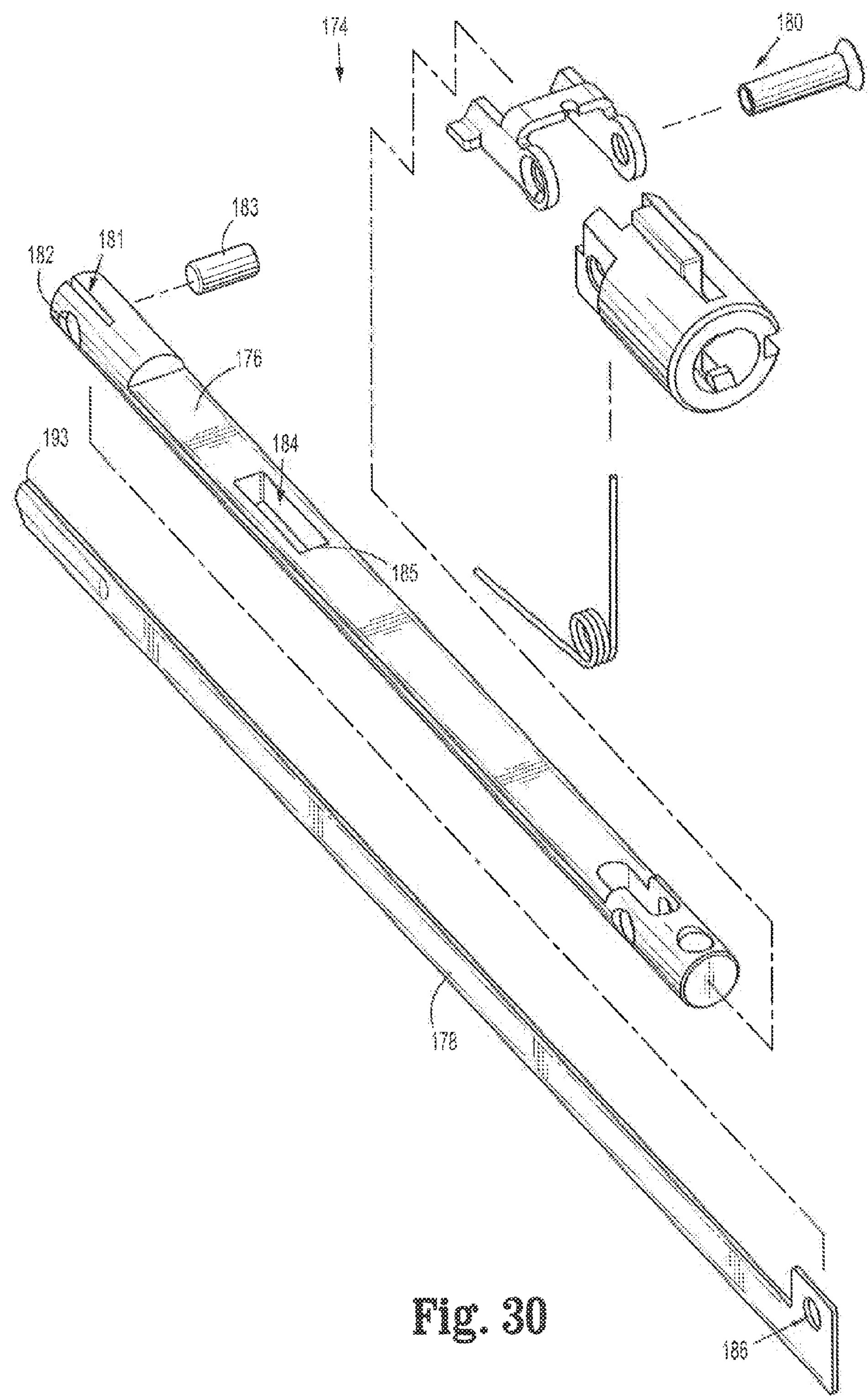
FIG. 30 is an exploded view of the sled pusher assembly shown in FIG. 29 with parts separated.
Figure 31:
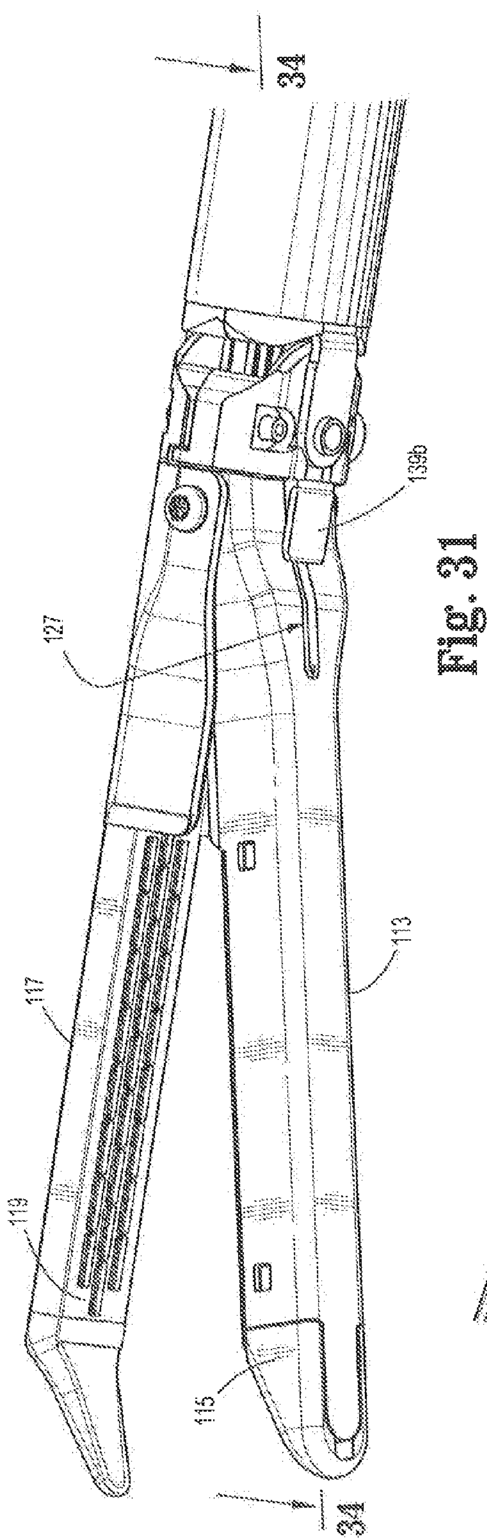
FIG. 31 is a partial, perspective view of the reload shown FIG. 21 with a distal end of the reload shown in an unclamped configuration.

Referring to FIGS. 29 and 30, a sled pusher assembly 174 is illustrated. The sled pusher assembly 174 includes an elongated support member 176 which has a distal end that engages a sled pusher 178 and a proximal end which supports a coupling assembly 180. The distal end of the support member 176 defines a slit 181 and a pair of apertures 182 (only one aperture 182 is shown). The apertures 182 extend through the slit 181 and receive a pin 183, rivet or the like. The slit 181 is configured to receive a proximal end of the sled pusher 178. The pin 183 extends through an aperture 186 defined through the proximal end of the sled pusher 178 to secure the sled pusher 178 to the support member 176. As can be appreciated other coupling methods could also be utilized to couple the sled pusher 178 to the support member 176.

Figure 33:
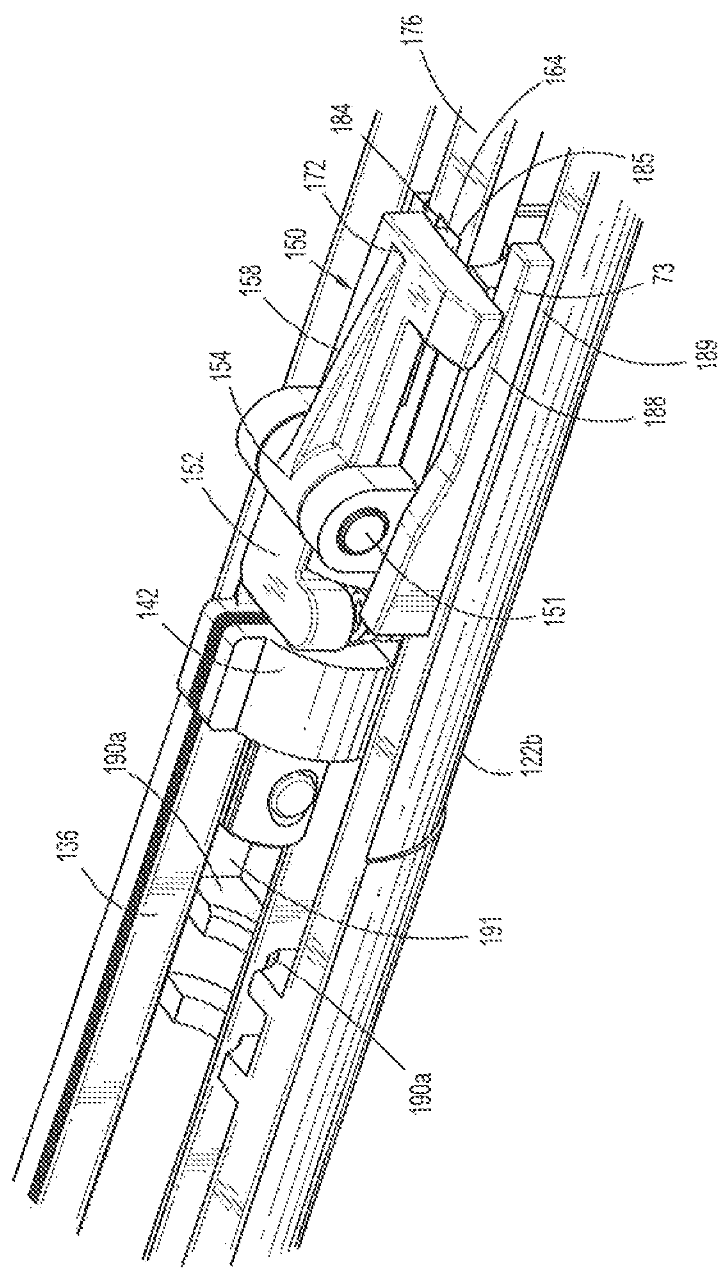
FIG. 33 is the indicated area of detail shown in FIG. 32.

An aperture 184 is provided on the support member 176. The aperture 184 is configured to receive the protrusion 164 of the latch 150 such that the protrusion 164 contacts a proximal wall portion 185 defining the aperture 184 (FIG. 33). In accordance with the instant disclosure, when the protrusion 164 is in contact with the proximal wall portion 185, the sled pusher assembly 174 and the and the drive beam assembly 134 are releasably coupled to one another such that movement of sled pusher assembly 174 effects corresponding movement of the drive beam assembly 134 to effect movement of the first jaw member 113 towards the second jaw member 117.

Figure 32:
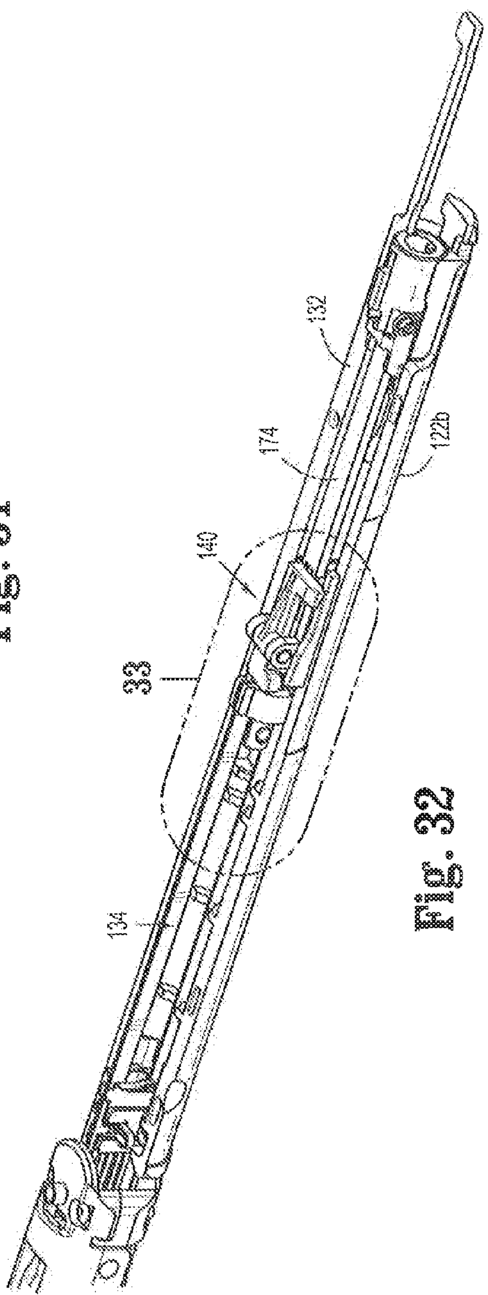
FIG. 32 is a partial, perspective view of the reload shown in FIG. 21 with parts removed illustrating the drive beam assembly and latch assembly when the distal end of the reload is in the unclamped configuration shown in FIG. 31.

Referring also to FIGS. 32 and 33, the lower housing portion 122*b* supports the drive assembly 134 including the latch assembly 140 and the sled pusher assembly 174. The lower housing portion 122*b* is configured to disengage the latch 150 of the latch assembly 140 from the sled pusher assembly 174 to allow further distal translation of the sled pusher assembly 174 independently of the drive beam assembly 134. Specifically, a ramp portion 188 is provided along a top wall 189 of the lower housing portion 122*b*. The ramp portion 188 is configured to contact the lateral offset extension 173 of the latch 150 to pivot the latch 150 about pivot member 151 to raise the protrusion 164 of the latch 150 out from engagement with the aperture 184 of the support member 176 of the sled pusher assembly 174 when the drive beam assembly 134 and sled pusher assembly 174 are translated distally to approximate the jaw members 113 and 117.

A pair of stops 190*a* are provided along an interior wall portion 191 of the lower housing portion 122*b*. Stops 190*a* are positioned to contact a lower portion of the collar 142 of the latch assembly 140 to prevent further distal translation of the drive beam assembly 134 after the collar 142 engages the stops 190*a*. In the illustrated embodiment, a corresponding pair of stops 190*b* (FIG. 39) is provided on the upper housing portion 122*a* and is configured to contact an upper portion of the collar 142 of the latch assembly 140 to prevent further distal translation of the drive beam assembly 134 after the collar 142 engages the stops 190*a*.

Figure 34:
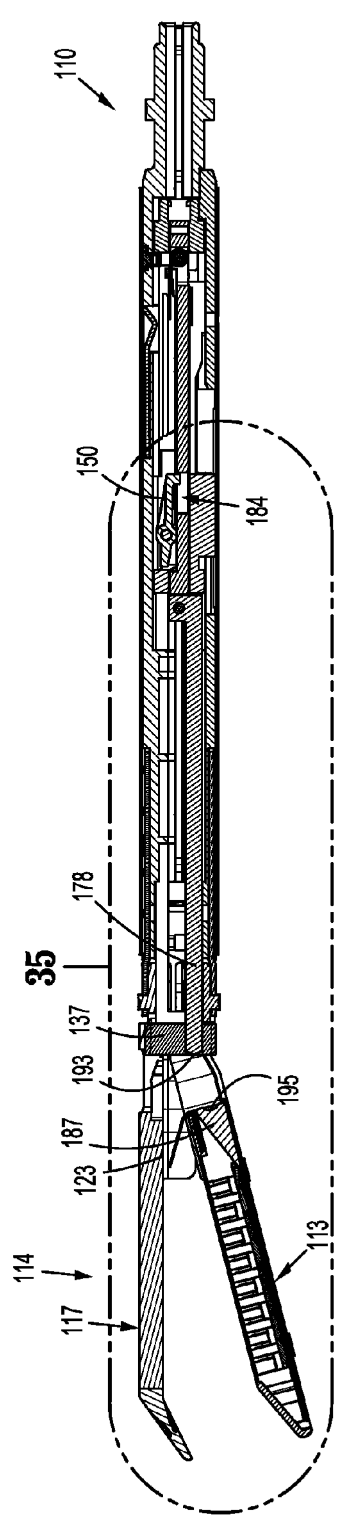
FIG. 34 is a cross sectional view taken along section line 34-34 in FIG. 31.
Figure 35:
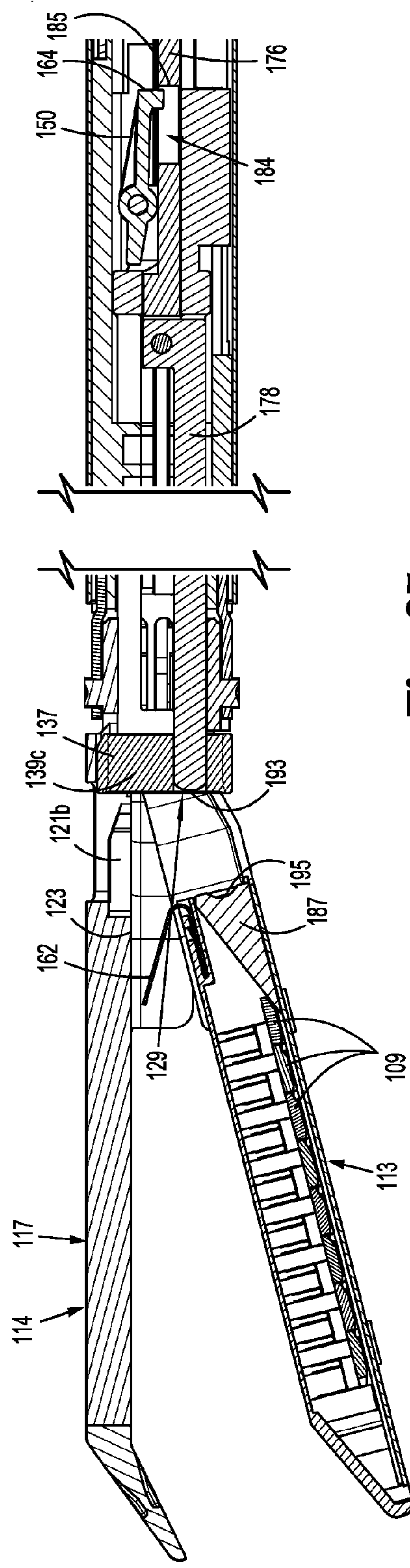
FIG. 35 is the indicated area of detail shown in FIG. 34.

FIGS. 34-44 illustrate the operation of the reload 110. Referring to FIGS. 33-35, prior to positioning tissue between the first and second jaw members 113, 117, the tool assembly 114 is urged to the spaced or unapproximated position by the resilient member 156 which contacts the interior wall 123 of the second jaw member 117 (FIGS. 34 and 35). In the spaced position, the protrusion 164 of the latch 150 is in contact with the proximal wall portion 185 defining the aperture 184 in the support member 176 to releasably couple the sled pusher assembly 174 to the drive beam assembly 134 such that distal translation of the sled pusher assembly 174 effects corresponding movement of the drive beam assembly 134.

In the spaced position of the jaw members 113 and 117, the distal end of the support member 176 is positioned through the longitudinal aperture 146 of the collar 142 of the latch assembly 140 and the sled pusher 178 is positioned within the notch 129 of strut 139*c* of the I-beam 137 to align a distal end 193 of the sled pusher 178 with a sled 187 that is provided in the cartridge 115 (FIG. 35). The distal end 193 of the sled pusher 178 is configured to engage a proximal end 195 of the sled 187 when the sled pusher 178 is translated distally into the cartridge 115. In the illustrated embodiment, the distal end 193 of the sled pusher 178 and the proximal end 195 of the sled 187 include complementary configurations, e.g., spherical configurations, to facilitate engagement therebetween. The sled 187 is configured to sequentially contact the plurality of pushers 109 to eject the plurality of fasteners 111 from the cartridge 115 as is known in the art.

Figure 36:
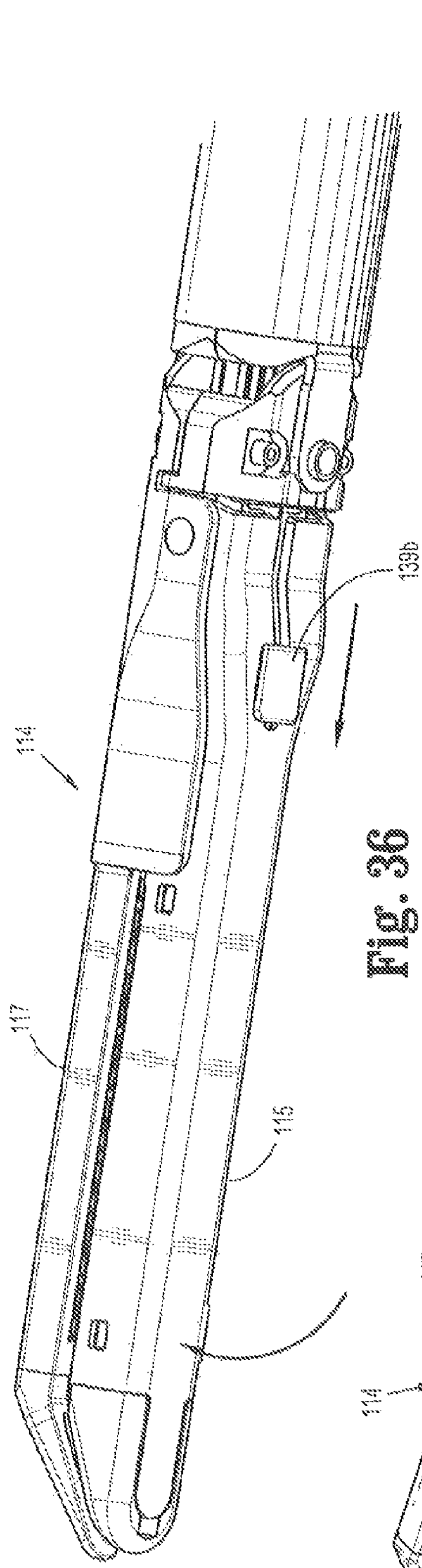
FIG. 36 is a partial, perspective view of the reload shown in FIG. 21 with a distal end of the reload shown in a clamped configuration.
Figure 37:
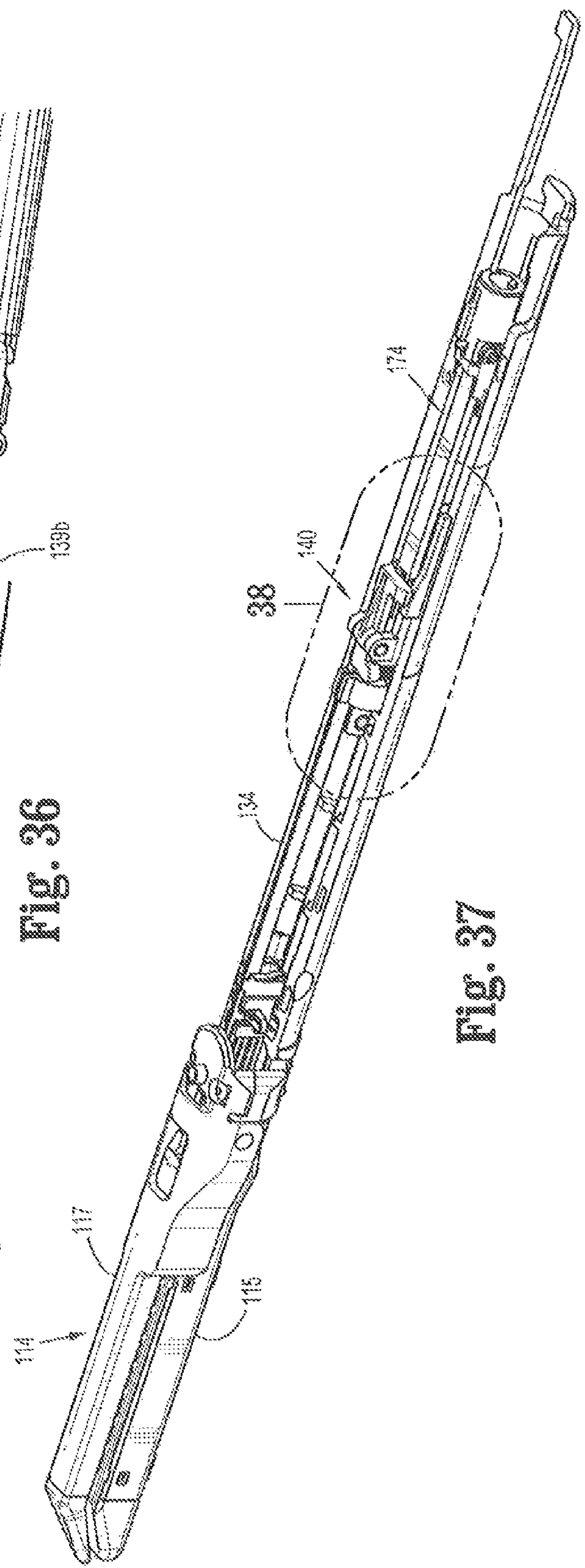
FIG. 37 is a partial, perspective view of the reload shown in FIG. 21 with parts removed illustrating the drive beam assembly and latch assembly when the distal end of the reload is in the clamped configuration shown in FIG. 36.
Figures 38, 39:
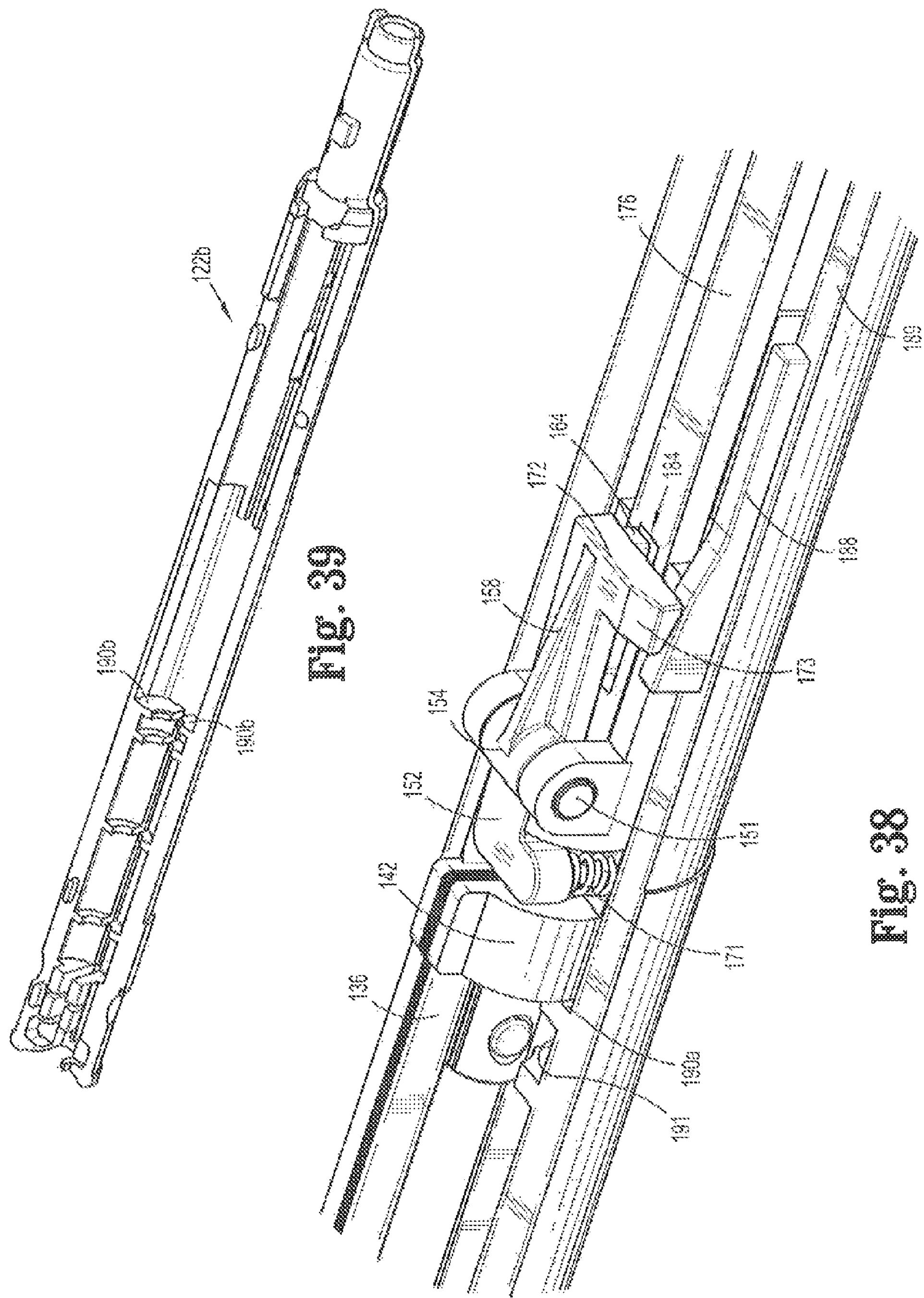
FIG. 38 is the indicated area of detail shown in FIG. 37.
FIG. 39 is a perspective view of an upper shaft portion of the reload shown in FIG. 21.

Referring to FIGS. 36-41, when the surgical actuating device 12 (FIG. 1B) is actuated to advance the sled pusher assembly 174, the drive assembly 134 which is releasably coupled to the sled pusher assembly 174 is advanced distally to move the I-beam 137 distally in relation to the tool assembly 114. As the I-beam is moved distally, the upper and lower flanges 139*a*, 139*b* of the I-beam 137 engage the first and second jaw members 113, 117, respectively, such that the first jaw member 113 is moved towards the second jaw member 117 to the clamped or approximated position of the tool assembly 114 to clamp tissue (FIG. 36). As noted above, the drive assembly 134 and the sled pusher assembly 174 move in unison as a result of the protrusion 164 being in contact with the proximal wall portion 185 defining the aperture 184 of the support member 176.

Figures 40, 41:
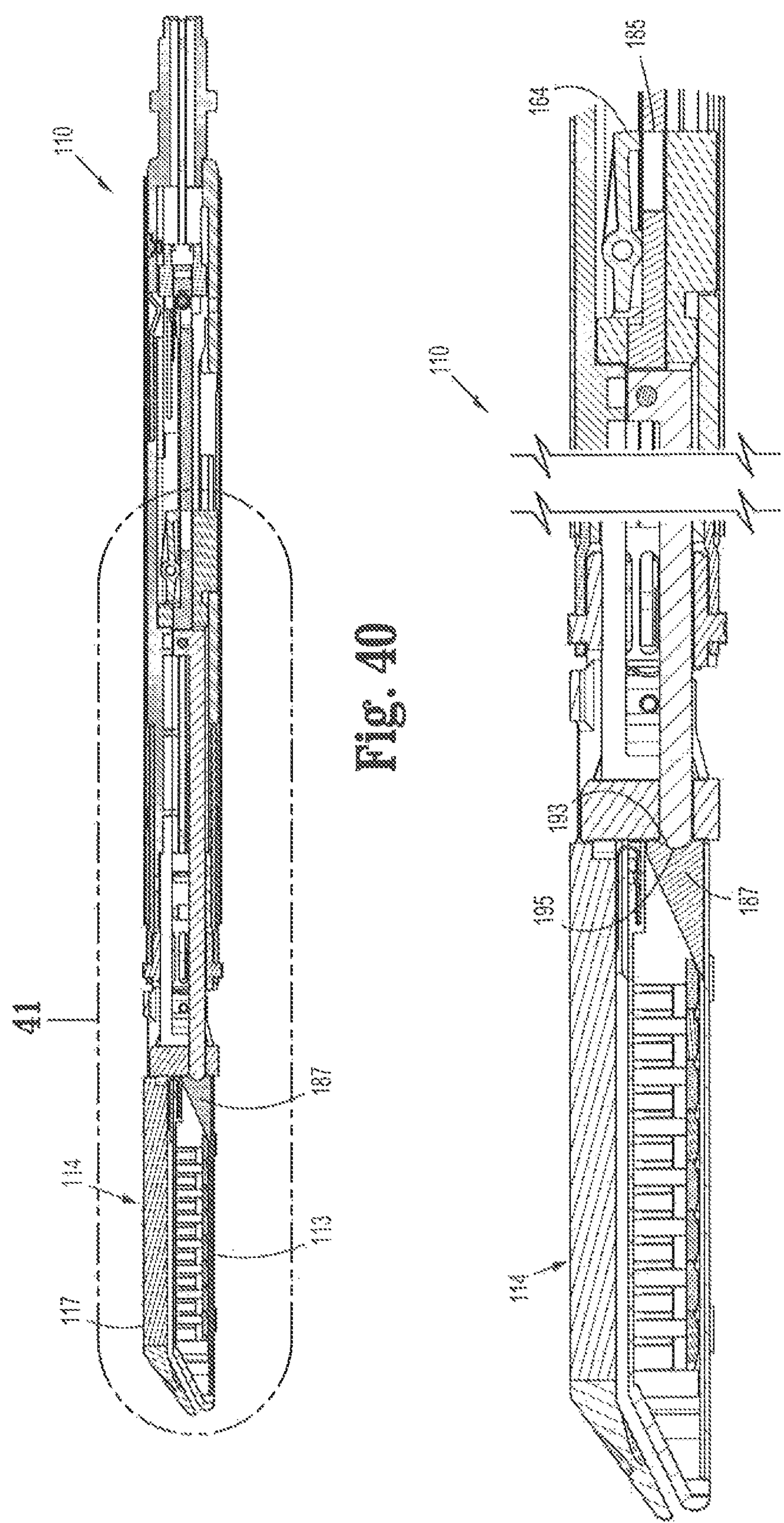
FIG. 40 is a cross sectional view of the reload shown in FIG. 21 with the distal end of the reload shown in the clamped configuration.
FIG. 41 is the indicated area of detail shown in FIG. 40.

As the drive assembly 134 is moved distally to move the jaw members 113 and 117 to the clamped or approximated position, the lateral offset 173 (FIG. 38) of the latch 150 slides up along the ramp 188 of the lower housing portion 122*b* and raises the latch 150 to disengage the protrusion 164 of the latch 140 from engagement with the proximal wall portion 185 of the support member 176. In the approximated position of the jaw members 113 and 117, the sled pusher assembly 174 is uncoupled from the drive assembly 134 and the distal end 193 of the sled pusher 178 is positioned in engagement with the proximal end 195 of the sled 187 (as best shown in FIG. 41).

In the approximated position, the collar 142 is in contact with the stops 190*a* in the lower housing portion 122*b* (FIGS. 38 and 42) and the upper portion of the collar 142 is in contact with the stops 190*b* in the upper housing portion 122*a*. Engagement between stops 190*a* and collar 142 prevents further distal movement of the drive beam assembly 134.

Figure 42:
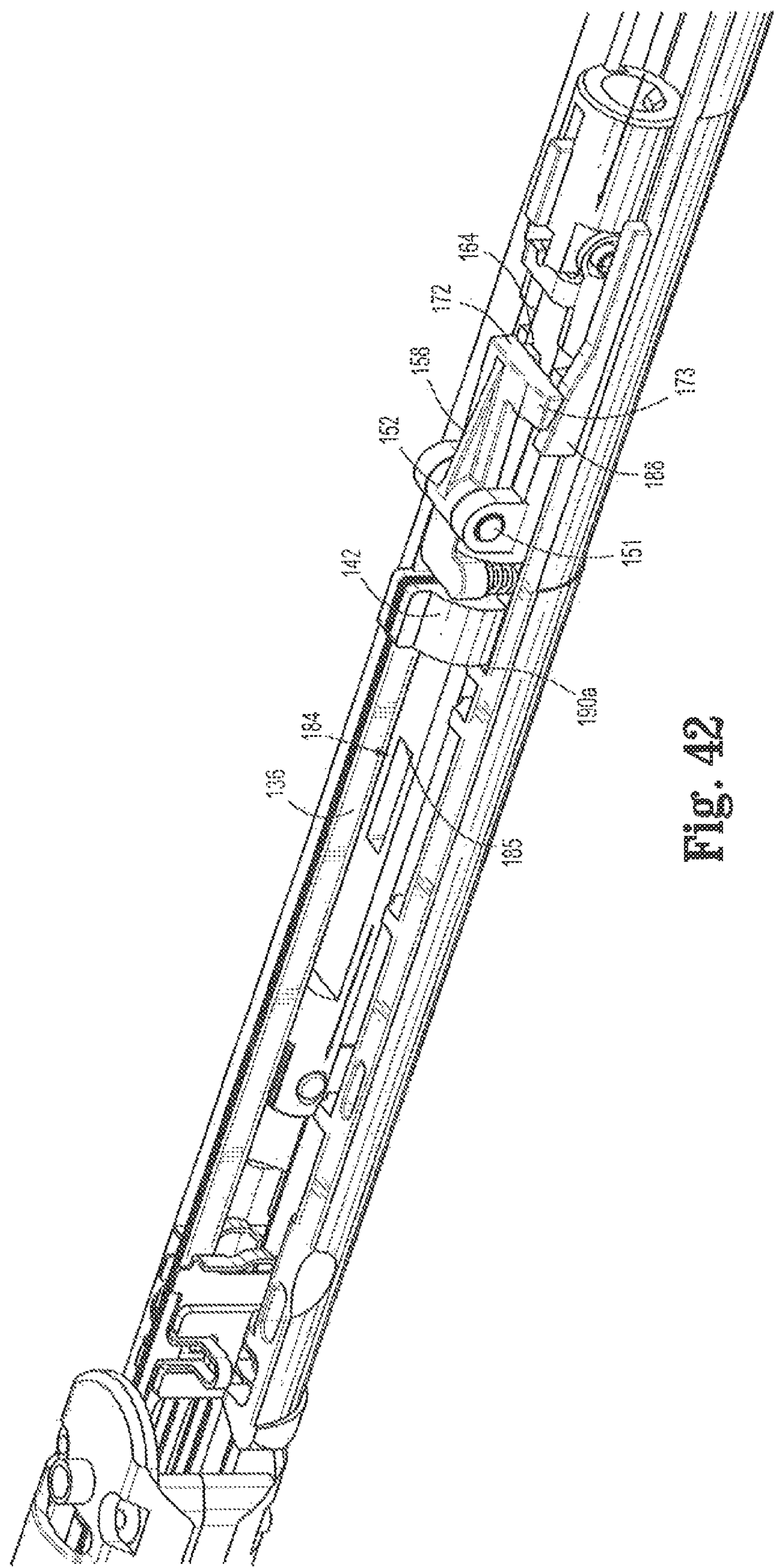
FIG. 42 is a partial, perspective view of the reload shown in FIG. 21 with parts removed illustrating the sled pusher assembly shown in FIG. 29 as the sled pusher assembly is being fired.
Figure 43:
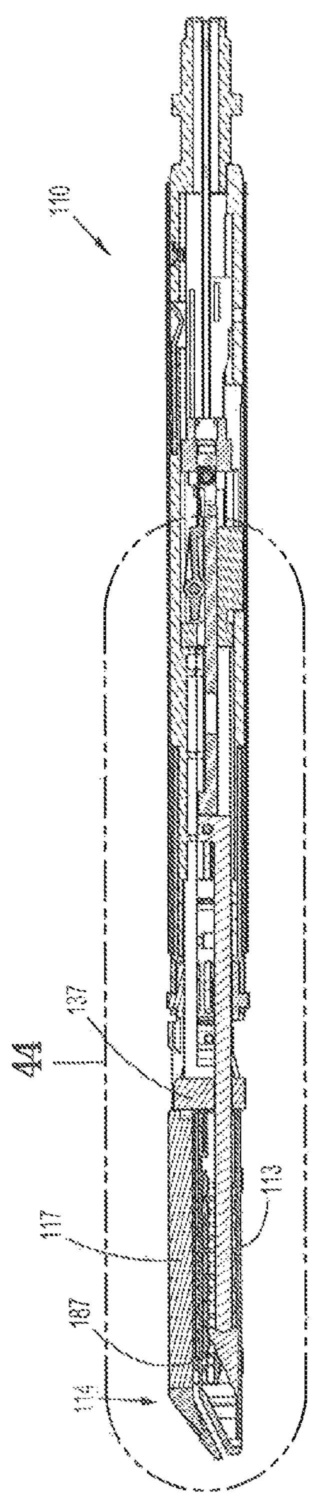
FIG. 43 is a cross sectional view of the reload shown in FIG. 21 with the reload shown in the clamped configuration and the sled pusher assembly being fired.
Figure 44:
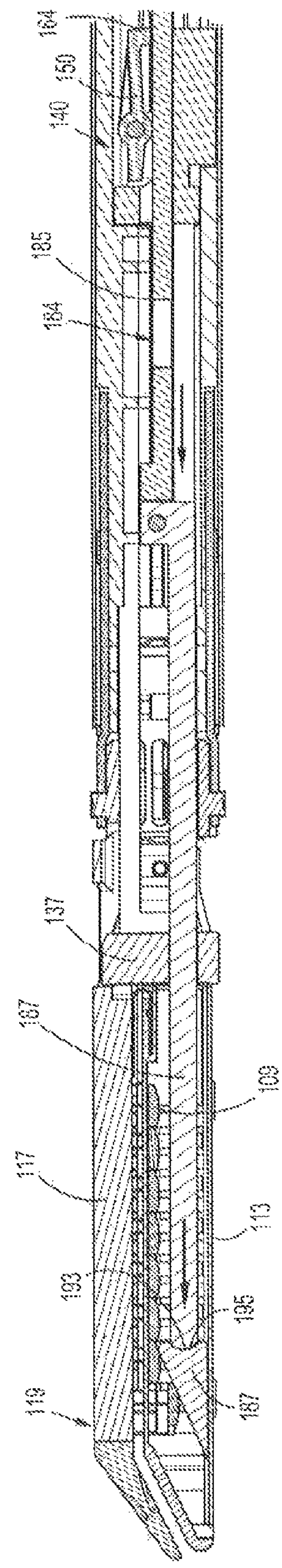
FIG. 44 is the indicated area of detail shown in FIG. 43.

Referring to FIGS. 42-44, after the sled pusher assembly 174 is uncoupled from the drive assembly 134, further actuation of the actuating device 12 effects independent movement of the sled pusher assembly 174 through the aperture 146 of the collar 142 such that the distal end 193 of the sled pusher 178 moves distally in relation to the I-beam 137 of the drive assembly 134 to advance the sled 187 through the cartridge 115 into sequential engagement with the pushers 109 to eject the plurality of fasteners 111 from the cartridge 115 (FIGS. 43 and 44).

While the reloads 10, 110 have been described herein as being configured for use with the stapler 212, it is within the purview of the present disclosure that the operative components of the reloads 10, 110 may be incorporated into a stapler with a tool assembly fixedly attached thereto.

The stapler 212 with either of the reloads 10, 110 attached thereto can be utilized to staple various tissue structures. For example, during a transplant procedure, where blood flow through vascular structure adjacent a transplant site needs to be controlled or inhibited, the stapler 212 can be utilized to staple (i.e., occlude) this vascular structure, thereby controlling and/or inhibiting blood flow through the vascular structure. It is contemplated that the stapler 212 with either of the reloads 10, 110 attached thereto can be utilized to staple other types of tissue structures and/or can be utilized in conjunction with other surgical procedures.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical stapling apparatus, comprising:

an actuating device including an elongated shaft;

a tool assembly disposed on a distal portion of the shaft, the tool assembly including a first jaw member supporting a cartridge assembly having a plurality of surgical fasteners, and a second jaw member supporting an anvil, the first jaw member being movable in relation to the second jaw member between a spaced position and an approximated position, the first jaw member including a cantilever at a proximal region of the first jaw member; and a firing cam bar assembly slidably disposed within the tool assembly, the firing cam bar assembly having a body including a distal portion, the body defining a cut-out including a cam surface having a first cam portion and a second cam portion, the second cam portion connected to and extending from the first cam portion, the cam surface configured to engage the cantilever to move the first jaw member towards the approximated position in relation to the second jaw member and the distal portion of the firing cam bar assembly configured to deploy the plurality of surgical fasteners from the cartridge assembly as the firing cam bar assembly is translated distally through the tool assembly.

2. The surgical stapling apparatus according to claim 1, wherein the body of the firing cam bar assembly includes a first firing cam bar having an elongated configuration, the first firing cam bar including a first part of the distal portion of the firing cam bar assembly and a first part of the cut-out defining the cam surface.

3. The surgical stapling apparatus according to claim 2, wherein the body of the firing cam bar assembly further includes a second firing cam bar having an elongated configuration, the second firing cam bar including a second part of the distal portion of the firing cam bar assembly and a second part of the cut-out defining the cam surface, the second firing cam bar seated within the first firing cam bar.

4. The surgical stapling apparatus according to claim 3, wherein the cartridge assembly includes a plurality of pushers and the distal portion of the firing cam bar assembly is configured to contact the plurality of pushers of the cartridge assembly to deploy the plurality of surgical fasteners from the cartridge assembly.

5. The surgical stapling apparatus according to claim 1, wherein the first cam portion is disposed distally and at an angle in relation to the second cam portion.

6. The surgical stapling apparatus according to claim 5, wherein the second cam portion of the cam surface tapers inwardly toward a proximal portion of the firing cam bar assembly.

7. The surgical stapling apparatus according to claim 1, wherein a resilient member is provided on the cartridge assembly for biasing the cartridge assembly radially away from the anvil such that a distal region of the cartridge assembly is spaced apart from a distal region of the anvil.

8. The surgical stapling apparatus according to claim 7, wherein the resilient member includes a proximal region and a distal region, the proximal region of the resilient member being coupled to a proximal region of the cartridge assembly, the distal region of the resilient member being positioned to contact at least a portion of the anvil.

9. The surgical stapling apparatus according to claim 8, wherein the proximal region of the resilient member includes two finger portions that are seated within two corresponding apertures defined at the proximal region of the cartridge assembly.

10. The surgical stapling apparatus according to claim 1, wherein the first jaw member includes the cantilever, the cantilever of the first jaw member is in the form of a bridge that extends transverse in relation to a longitudinal axis defined through the shaft of the surgical stapling apparatus.

11. The surgical stapling apparatus according to claim 1, wherein the tool assembly is removably couplable to the distal portion of the shaft of the surgical stapling apparatus.

12. The stapling apparatus according to claim 1, wherein the cut-out having the cam surface is disposed proximal to the distal portion of the firing cam bar assembly and spaced-apart from the distal portion of the firing cam bar assembly.

13. A reload configured for use with a surgical stapling apparatus, the reload comprising:

a shaft including a proximal portion and distal portion, the proximal portion adapted to couple to a surgical apparatus;

a tool assembly disposed on the distal portion of the shaft, the tool assembly including a first jaw member supporting a cartridge assembly having a plurality of surgical fasteners, and a second jaw member supporting an anvil, the first jaw member being movable in relation to the second jaw member between a spaced position and an approximated position, one of the first and second jaw members including a cantilever at a proximal region of the first and second jaw members; and a firing cam bar assembly defining a longitudinal axis, the firing cam bar assembly slidably disposed within the tool assembly, the firing cam bar assembly including a cam surface having a first cam portion and a second cam portion, the second cam portion connected to and extending from the first cam portion and including a taper relative to the longitudinal axis, the cam surface configured to engage the cantilever to move the first jaw member towards the approximated position in relation to the second jaw member, wherein the taper of the second cam portion determines a gap distance between the first jaw member and the second jaw member in the approximated position, the firing cam bar assembly including a distal portion, the distal portion of the firing cam bar assembly configured to deploy the plurality of surgical fasteners from the cartridge assembly as the firing cam bar assembly is translated distally through the tool assembly.

14. The reload according to claim 13, wherein the firing cam bar assembly includes a body having a first firing cam bar having an elongated configuration, the body defining a cut-out defining the cam surface.

15. The reload according to claim 14, wherein the body of the firing cam bar assembly further includes a second firing cam bar having an elongated configuration, the second firing cam bar including the cut-out defining the cam surface, the second firing cam bar seated within the first firing cam bar.

16. The reload according to claim 15, wherein the cartridge assembly includes a plurality of pushers, the distal portion of the firing cam bar assembly defined by a first distal section of the first firing cam bar and a second distal section of the second firing cam bar, the first and second distal sections of the first and second firing cam bars configured to contact the plurality of pushers of the cartridge assembly to deploy the plurality of surgical fasteners from the cartridge assembly.

17. The reload according to claim 13, wherein the first cam portion is disposed distally and at an angle in relation to the second cam portion.

18. The reload according to claim 17, wherein the second cam portion of the cam surface tapers inwardly toward a proximal portion of the firing cam bar assembly.

19. The reload according to claim 13, wherein a resilient member is provided on the cartridge assembly for biasing the cartridge assembly radially away from the anvil such that a distal region of the cartridge assembly is spaced apart from a distal region of the anvil.

20. The reload according to claim 19, wherein the resilient member includes proximal and distal regions, the proximal region of the resilient member being coupled to a proximal region of the cartridge assembly, the distal region of the resilient member being positioned to contact at least a portion of the anvil.

21. The reload according to claim 20, wherein the proximal region of the resilient member includes two finger portions that are seated within two corresponding apertures defined at the proximal region of the cartridge assembly.

22. The reload according to claim 13, wherein the first jaw member includes the cantilever, the cantilever of the first jaw member is in the form of a bridge that extends transverse in relation to a longitudinal axis defined through the shaft of the reload.

* * * * *